(12) United States Patent
Swager et al.

(10) Patent No.: US 12,061,194 B2
(45) Date of Patent: *Aug. 13, 2024

(54) SYSTEMS INCLUDING JANUS DROPLETS WITH BINDING MOIETIES FOR A VIRUS, A PATHOGEN OR A BACTERIUM

(71) Applicant: Massachusetts Institute of Technology, Cambridge, MA (US)

(72) Inventors: Timothy Manning Swager, Newton, MA (US); Hadley Sikes Johnson, Arlington, MA (US); Qifan Zhang, Revere, MA (US); Eric Alexander Miller, Somerville, MA (US); Lukas Zeininger, Berlin (DE); Ki-Joo Sung, Minneapolis, MN (US); Kosuke Yoshinaga, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/545,979

(22) Filed: Dec. 8, 2021

(65) Prior Publication Data

US 2022/0205989 A1 Jun. 30, 2022

Related U.S. Application Data

(63) Continuation of application No. 16/202,007, filed on Nov. 27, 2018, now abandoned, which is a
(Continued)

(51) Int. Cl.
*G01N 21/77* (2006.01)
*C12Q 1/6834* (2018.01)
(Continued)

(52) U.S. Cl.
CPC ....... *G01N 33/5432* (2013.01); *C12Q 1/6834* (2013.01); *C12Q 1/701* (2013.01);
(Continued)

(58) Field of Classification Search
CPC .............................. G01N 21/77; G01N 33/543
(Continued)

(56) References Cited

U.S. PATENT DOCUMENTS 3,826,613 A * 7/1974 Thomas .................... C12Q 1/70
435/5
4,663,277 A * 5/1987 Wang .................... G01N 33/545
436/805
(Continued)

FOREIGN PATENT DOCUMENTS

EP 135352 A * 3/1985 ........... C07K 14/005
EP 161328 A * 11/1985 ............... C12N 7/00
(Continued)

OTHER PUBLICATIONS

Anker, J. N. et al, Applied Physics Letters 2003, 82, 1102-1104 (Year: 2003).*
(Continued)

*Primary Examiner* — Arlen Soderquist
(74) *Attorney, Agent, or Firm* — Wolf, Greenfield & Sacks, P.C.

(57) ABSTRACT

Embodiments described herein may be useful in the detection of analytes. The systems and methods may allow for a relatively simple and rapid way for detecting analytes such as chemical and/or biological analytes and may be useful in numerous applications including sensing, food manufacturing, medical diagnostics, performance materials, dynamic lenses, water monitoring, environmental monitoring, detection of proteins, detection of DNA, among other applications. For example, the systems and methods described
(Continued)

herein may be used for determining the presence of a contaminant such as bacteria (e.g., detecting pathogenic bacteria in food and water samples which helps to prevent widespread infection, illness, and even death). Advantageously, the systems and methods described herein may not have the drawbacks in current detection technologies including, for example, relatively high costs, long enrichment steps and analysis times, and/or the need for extensive user training. Another advantageous feature provided by the systems and methods described herein includes fabrication in a relatively large scale. In some embodiments, the systems and methods may be used in conjunction with a detector including handheld detectors incorporated with, for example, smartphones (e.g., for the on-site detection of analytes such as pathogenic bacteria).

16 Claims, 19 Drawing Sheets

Related U.S. Application Data continuation-in-part of application No. 16/113,520, filed on Aug. 27, 2018, now abandoned, which is a continuation of application No. 15/269,543, filed on Sep. 19, 2016, now Pat. No. 10,060,913.

(51) Int. Cl.
*C12Q 1/70* (2006.01)
*G01N 21/59* (2006.01)
*G01N 33/543* (2006.01)
*G01N 33/569* (2006.01)
*G01N 21/78* (2006.01)

(52) U.S. Cl.
CPC ............. *G01N 21/59* (2013.01); *G01N 21/77* (2013.01); *G01N 33/54366* (2013.01); *G01N 33/56983* (2013.01); *G01N 2021/7783* (2013.01); *G01N 21/78* (2013.01); *G01N 2201/0221* (2013.01)

(58) Field of Classification Search
USPC .................... 436/63, 501, 523; 422/82.05
See application file for complete search history.

(56) References Cited

U.S. PATENT DOCUMENTS

| | | |
|---|---|---|
| 4,870,026 A | 9/1989 | Wands et al. |
| 4,912,034 A | 3/1990 | Kalra et al. |
| 5,066,465 A | 11/1991 | Kano et al. |
| 5,217,648 A | 6/1993 | Beissinger et al. |
| 5,332,661 A | 7/1994 | Adamczyk et al. |
| 5,387,676 A | 2/1995 | Zavada et al. |
| 5,516,635 A | 5/1996 | Ekins et al. |
| 5,980,936 A | 11/1999 | Krafft et al. |
| 6,180,418 B1 | 1/2001 | Lee |
| 6,271,202 B1 | 8/2001 | Kudsk |
| 6,710,092 B2 | 3/2004 | Scher et al. |
| 7,067,590 B2 | 6/2006 | Sato et al. |
| 7,625,951 B2 | 12/2009 | Daunert et al. |
| 7,767,017 B2 | 8/2010 | Lahann et al. |
| 7,947,772 B2 | 5/2011 | Lahann et al. |
| 8,241,651 B2 | 8/2012 | Lahann |
| 9,415,392 B2 | 8/2016 | Ismagilov et al. |
| 10,005,058 B2 | 6/2018 | Swager et al. |
| 10,060,913 B2 | 8/2018 | Swager et al. |
| 10,252,231 B2 | 4/2019 | Swager et al. |
| 11,119,098 B2 | 9/2021 | Swager et al. |
| 11,229,892 B2 | 1/2022 | Swager et al. |
| 2002/0040065 A1 | 4/2002 | Scher et al. |
| 2002/0090608 A1 | 7/2002 | Palese et al. |
| 2004/0069857 A1 | 4/2004 | Leblans et al. |
| 2004/0176479 A1 | 9/2004 | Scher et al. |
| 2006/0154234 A1 | 7/2006 | Winther et al. |
| 2006/0201390 A1 | 9/2006 | Lahann et al. |
| 2007/0105972 A1* | 5/2007 | Doyle ................. B81C 99/0095 522/1 |
| 2007/0237800 A1 | 10/2007 | Lahann et al. |
| 2008/0234394 A1* | 9/2008 | Hong ...................... B01J 13/00 516/22 |
| 2008/0242774 A1 | 10/2008 | Lahann et al. |
| 2009/0232856 A1 | 9/2009 | Patel |
| 2009/0306311 A1 | 12/2009 | Reed |
| 2010/0062525 A1 | 3/2010 | Abbott et al. |
| 2010/0069726 A1 | 3/2010 | Levinson |
| 2010/0097687 A1 | 4/2010 | Lipovetskaya et al. |
| 2010/0099048 A1* | 4/2010 | Thomas ................. G03F 7/2035 355/71 |
| 2011/0003401 A1* | 1/2011 | Oscarsson ............ B01J 19/0046 506/13 |
| 2011/0104777 A1 | 5/2011 | Marquez et al. |
| 2011/0195394 A1 | 8/2011 | Selinfreund et al. |
| 2011/0195421 A1 | 8/2011 | Selinfreund et al. |
| 2011/0196085 A1 | 8/2011 | Selinfreund et al. |
| 2011/0223590 A1 | 9/2011 | Chiou et al. |
| 2012/0028342 A1 | 2/2012 | Ismagilov et al. |
| 2012/0045748 A1* | 2/2012 | Willson ............... C12Q 1/6804 435/6.12 |
| 2012/0248020 A1 | 10/2012 | Granick et al. |
| 2012/0288852 A1* | 11/2012 | Willson ................. G01N 15/10 436/71 |
| 2012/0319043 A1 | 12/2012 | Stepien et al. |
| 2012/0328654 A1 | 12/2012 | Huang et al. |
| 2014/0016177 A1 | 1/2014 | Aizenberg et al. |
| 2014/0227684 A1 | 8/2014 | Hindson et al. |
| 2014/0323330 A1* | 10/2014 | Bergo ................ G01N 33/6851 506/18 |
| 2014/0350168 A1 | 11/2014 | Bormashenko |
| 2015/0238636 A1 | 8/2015 | Homyk et al. |
| 2016/0114325 A1* | 4/2016 | Tang ................. B01L 3/502761 436/180 |
| 2016/0151753 A1 | 6/2016 | Swager et al. |
| 2016/0151756 A1 | 6/2016 | Swager et al. |
| 2016/0193602 A1* | 7/2016 | Tsai ...................... B01L 3/5085 436/86 |
| 2016/0235670 A1 | 8/2016 | Mason et al. |
| 2017/0368865 A1 | 12/2017 | Macpherson et al. |
| 2017/0371151 A1 | 12/2017 | Brassard et al. |
| 2018/0080927 A1 | 3/2018 | Swager et al. |
| 2019/0170736 A1 | 6/2019 | Swager et al. |
| 2019/0170737 A1 | 6/2019 | Swager et al. |
| 2019/0184356 A1 | 6/2019 | Swager et al. |
| 2019/0212333 A1 | 7/2019 | Swager et al. |
| 2020/0166503 A1 | 5/2020 | Swager et al. |
| 2021/0041425 A1 | 2/2021 | Swager et al. |
| 2021/0080456 A1* | 3/2021 | Swager ................ C01B 33/145 |
| 2022/0205989 A1* | 6/2022 | Swager .................. C12Q 1/701 |

FOREIGN PATENT DOCUMENTS

| | | | |
|---|---|---|---|
| EP | 323909 A * | 7/1989 | ......... G01N 33/5306 |
| EP | 1365240 A2 * | 11/2003 | ....... G01N 33/54313 |
| JP | 05099926 A * | 4/1993 | |
| JP | 2013-518167 | 5/2013 | |
| WO | WO-9214154 A1 * | 8/1992 | ......... G01N 33/54313 |
| WO | WO 1992/17179 A1 | 10/1992 | |
| WO | WO 1995/31500 A2 | 11/1995 | |
| WO | WO-2004063707 A2 * | 7/2004 | ............... C12Q 1/04 |
| WO | WO-2008066463 A1 * | 6/2008 | ......... C07K 14/4716 |
| WO | WO 2009/061372 A1 | 5/2009 | |
| WO | WO 2009/101113 A2 | 8/2009 | |
| WO | WO-2009151390 A1 * | 12/2009 | ........... G01N 33/559 |
| WO | WO-2010092333 A1 * | 8/2010 | ....... G01N 33/54346 |
| WO | WO 2011/093733 A1 | 8/2011 | |
| WO | WO 2013/059294 A1 | 4/2013 | |

(56) References Cited

FOREIGN PATENT DOCUMENTS

| WO | WO 2015/051179 A1 | 4/2015 |
|---|---|---|
| WO | WO 2016/103226 A2 | 6/2016 |

OTHER PUBLICATIONS

McNaughton, B. H. et al, Journal of Magnetism and Magnetic Materials 2009321, 1648-1652. (Year: 2009).*
Erb, R. M. et al., Advanced Materials 2009, 21, 4825-4829. (Year: 2009).*
Yin, S.-N. et al, Advanced Materials 2011, 23, 2915-2919. (Year: 2011).*
McNaughton, B. H. et al, Applied Physics Letters 2007, 97, paper 224105, 3 pages. (Year: 2007).*
Yu, H. et al, Current Pharmaceutical Biotechnology 2015, 16, 716-723. (Year: 2015).*
International Search Report and Written Opinion mailed Jan. 22, 2016 for Application No. PCT/US2015/058268.
International Preliminary Report on Patentability mailed May 11, 2017 for Application No. PCT/US2015/058268.
Extended European Search Report mailed Jun. 11, 2018 for Application No. EP 15855674.6.
International Search Report and Written Opinion mailed Nov. 30, 2017 for Application No. PCT/US2017/052209.
International Preliminary Report on Patentability mailed Mar. 28, 2019 for Application No. PCT/US2017/052209.
[No Author Listed], Definition of Associate. Retrieved from https://www.vocabulary.com/associate. Accessed on Apr. 22, 2020. 4 pages.
[No Author Listed], Definition of Fluidic. Retrieved from https://www.merriam-webster.com/dictionary/fluidic. Last accessed on Apr. 14, 2021. 10 pages.
Alino et al., Liquid crystal droplets as a hosting and sensing platform for developing immunoassays. Langmuir. Aug. 2011;27:11784-9.
Augustin et al., Nano- and micro-structured assemblies for encapsulation of food ingredients. Chem Soc Rev. Apr. 2009;38(4):902-12. doi: 10.1039/b801739p. Epub Dec. 4, 2008.
Axenov et al., Thermotropic Ionic Liquid Crystals. Materials. 2011;4:206-59. Epub Jan. 14, 2011.
Bedford et al., Solubilities and Volume Changes Attending Mixing for the System: Perfluoro-n-hexane-n-Hexane. J. Am. Chem. Soc., 1958, 80(2): 282-285.
Belmonte et al., Patterned Full-Color Reflective Coatings Based on Photonic Cholesteric Liquid-Crystalline Particles. ACS Appl Mater Interfaces. Apr. 17, 2019;11(15):14376-14382. doi: 10.1021/acsami.9b02680. Epub Apr. 8, 2019.
Berger et al., Stimuli-responsive bicomponent polymer Janus particles by "grafting from"/"grafting to" approaches. Macromolecules. 2008;41:9669-76. Epub Nov. 21, 2008.
Besnard et al., Multiple emulsions controlled by stimuli-responsive polymers. Adv Mater. May 28, 2013;25(20):2844-8. doi: 10.1002/adma.201204496. Epub Mar. 11, 2013.
Bijlard et al., Functional Colloidal Stabilization. Advanced Materials Interfaces. Jan. 2019;4(1):1600443. Epub Nov. 8, 2016. 31 pages.
Brake et al., Biomolecular interactions at phospholipid-decorated surfaces of liquid crystals. Science. Dec. 19, 2003;302(5653):2094-7. doi: 10.1126/science.1091749.
Braun et al., Functional liquid crystalline particles and beyond. Liquid Crystals. 2019;46(13-14):2023-41.
Broer et al., Functional organic materials based on polymerized liquid-crystal monomers: supramolecular hydrogen-bonded systems. Angew Chem Int Ed Engl. Jul. 16, 2012;51(29):7102-9. doi: 10.1002/anie.201200883. Epub May 15, 2012.
Brown et al., Stimuli-responsive surfactants. Soft Matter 2013; 9:2365-2374.
Brunsveld et al., Hierarchical Growth of Chiral Self-Assembled Structures in Protic Media. J. Am. Chem. Soc. 2000;122(26):6175-82. Epub Jun. 17, 2000.

Chakravarti et al., Liquid membrane multiple emulsion process of chromium(VI) separation from waste waters. Colloid Surface A 1995; 103:59-71.
Chen et al., Janus particles templated from double emulsion droplets generated using microfluidics. Langmuir. 2009;25(8):4320-3. Epub Mar. 18, 2009.
Chen et al., Photoresponsive Monodisperse Cholesteric Liquid Crystalline Microshells for Tunable Omnidirectional Lasing Enabled by a Visible Light-Driven Chiral Molecular Switch. Adv Op Mat 2014; 2(9): 845-8.
Chevallier et al., Photofoams: remote control of foam destabilization by exposure to light using an azobenzene surfactant. Langmuir. Feb. 7, 2012;28(5):2308-12. doi: 10.1021/la204200z. Epub Jan. 27, 2012.
Choi et al., Microfluidic Design of Complex Emulsions. ChemPhysChem 2014; 15: 21-290.
Choi et al., One step formation of controllable complex emulsions: from functional particles to simultaneous encapsulation of hydrophilic and hydrophobic agents into desired position. Adv mater. 2013; 6 pages.
Choi et al., Patterned fluorescent particles as nanoprobes for the investigation of molecular interactions. Nano Letters. 2003;3(8):995-1000. Epub Jul. 11, 2003.
Cipparrone et al., Chiral self-assembled solid microspheres: a novel multifunctional microphotonic device. Adv Mater. Dec. 22, 2011;23(48):5773-8. doi: 10.1002/adma.201102828. Epub Nov. 15, 2011.
Concellón et al., Dynamic Complex Liquid Crystal Emulsions. J. Am. Chem. Soc. 2019;141(45):18246-55. Epub Nov. 1, 2019.
Craig et al., Effect of Spacer Length on the Thermal Properties of Side-Chain Liquid Crystal Polymethacrylates. 2. Synthesis and Characterization of the Poly[omega-(4'-cyanobiphenyl-4-yloxy)alkyl methacrylate]s. Macromolecules. 1995;28(10):3617-24. Epub May 1, 1995.
De La Fuente et al., Exploring the efficiency of gallic acid-based dendrimers and their block copolymers with PEG as gene carriers. Nanomed. 2012;7(11):1667-81. Epub Jul. 20, 2012.
Dominguez et al., Modelling and understanding of the vapour-liquid and liquid-liquid interfacial properties for the binary mixture of n-heptane and perfluoro-n-hexane. J. Mol. Liq. 2013; 185:36-43.
Engel et al., Insulin: intestinal absorption as water-in-oil-in-water emulsions. Nature. Aug. 24, 1968;219(5156):856-7.
Eremin et al., Azodendrimers as a photoactive interface for liquid crystals. Liquid Crystals. 2018;45(13-15):2121-31. Epub Aug. 17, 2018.
Fleischmann et al., One-piece micropumps from liquid crystalline core-shell particles. Nat Commun. 2012;3:1178. doi: 10.1038/ncomms2193. Epub Nov. 6, 2012. 8 pages.
Forth et al., Building Reconfigurable Devices Using Complex Liquid-Fluid Interfaces. Advanced Materials. May 2019;31(18):1806370. Epub Mar. 4, 2019. 39 pages.
Gao et al., Double Emulsion Templated Microcapsules with Single Hollow Cavities and Thickness-Controllable Shells. Langmuir, 2009, 25(6): 3832-3838.
Ge et al., Droplet topology control of Janus emulsion prepared in one-step high energy mixing. Soft Matter. 2014;10:4498-505. Epub Apr. 8, 2014.
Ge et al., Recent studies of Janus emulsions prepared by one-step vibrational mixing. Current Opinion in Colloid & Interface Science. Oct. 2016;25:58-66.
Gladysz et al., Structural, physical, and chemical properties of fluorous compounds. Top Curr Chem. 2012;308:1-23. doi: 10.1007/128_2011_282.
Gresham et al., Use of a sustained-release multiple emulsion to extend the period of radio protection conferred by cysteamine. Nature. Nov. 19, 1971;234(5325):149-50.
Guzowski et al., The structure and stability of multiple microdroplets. Soft Matter 2012; 8: 7269-7278.
Haase et al., Tailoring of high-order multiple emulsions by the liquid-liquid phase separation of ternary mixtures. Angew Chem Int Ed. 2014;53:1-6.

(56) References Cited

OTHER PUBLICATIONS

Han et al., Retroreflective Janus microparticle as a nonspectroscopic optical immunosensing probe. ACS Appl Mater & Interfaces. May 4, 2016;8(17):10767-74.
He et al., Interfacial Polymerization on Dynamic Complex Colloids: Creating Stabilized Janus Droplets. ACS Applied Materials & Interfaces. 2017;9(8):7804-11. Epub Feb. 15, 2017.
Heinze et al., Microfluidic immunosensor for rapid and sensitive detection of bovine viral diarrhea virus. Sensors and Actuators B. 2009;138:491-6.
Hessberger et al., Interfacial Self-Assembly of Amphiphilic Dual Temperature Responsive Actuating Janus Particles. Adv Funct Mater. 2018;28(21):1800629. 10 pages.
Jampani et al., Micrometer-Scale Porous Buckling Shell Actuators Based on Liquid Crystal Networks. Advanced Functional Materials. 2018;28(31):1801209. Epub Jun. 5, 2018. 9 pages.
Jeong et al., Liquid crystal Janus emulsion droplets: preparation, tumbling, and swimming. Soft Matter. Sep. 14, 2015;11(34):6747-54. doi: 10.1039/c5sm01053e. Epub Jul. 14, 2015.
Joyce, Fluidics—Basic Components and Applications. U.S. Army Electronics Research and Development Command. Harry Diamond Laboratories. Adelphi, MD. Aug. 1983. 24 pages.
Kang et al., Amplified Photon Upconversion by Photonic Shell of Cholesteric Liquid Crystals. J Am Chem Soc. Apr. 26, 2017;139(16):5708-5711. doi: 10.1021/jacs.7b01981. Epub Apr. 17, 2017.
Kato et al., Functional Liquid Crystals towards the Next Generation of Materials. Angew Chem Int Ed Engl. Apr. 9, 2018;57(16):4355-4371. doi: 10.1002/anie.201711163. Epub Mar. 13, 2018.
Kaufmann et al., "Sandwich" microcontact printing as a mild route towards monodisperse Janus particles with tailored bifunctionality. Adv Mater. 2011;23:79-83; Supporting Information pp. 1-8.
Kaufmann et al., Bifunctional Janus beads made by "sandwich" microcontact printing using click chemistry. J Mater Chem. 2012;22:6190-9. Epub Feb. 17, 2012. Electronic suppl info pp. 1-9.
Kim et al., Fabrication of monodisperse gel shells and functional microgels in microfluidic devices. Angew Chem Int Ed Engl. 2007;46(11):1819-22.
Kumar et al., Multiple emulsions: a review. Int J Rec Adv Pharm Rsch. Jan. 2012; 2(1):9-19.
Lemal, Perspective on fluorocarbon chemistry. J Org Chem. Jan. 9, 2004;69(1):1-11.
Li et al., Synthesis of biofunctional Janus particles. Macromol Rapid Comm. 2015;36:1200-4.
Lin et al., Endotoxin-Induced Structural Transformations in Liquid Crystalline Droplets. Science. Jun. 10, 2011; 332(6035): 1297-1300. Epub May 19, 2011. Author manuscript provided. 8 pages.
Lin et al., Morphology-Dependent Luminescence in Complex Liquid Colloids. J Am Chem Soc. Mar. 6, 2019;141(9):3802-3806. doi: 10.1021/jacs.8b13215. Epub Feb. 20, 2019. Author manuscript provided. 16 pages.
Lone et al., Fabrication of polymeric Janus particles by droplet microfluidics. RSC Adv. 2014 4: 13322-13333.
McClain et al., Interfacial roughness in a near-critical binary fluid mixture: X-ray reflectivity and near-specular diffuse scattering. Eur. Phys. J. B. 1999; 10: 45-52.
McClements et al., Factors that affect the rate of oil exchange between oil-in-water emulsion droplets stabilized by a nonionic surfactant: Droplet size, surfactant concentration, and ionic strength. J. Phys. Chem. Jun. 1993; 97(28): 7304-08. doi: 10.1021/j100130a030.
McClements et al., Structured emulsion-based delivery systems: controlling the digestion and release of lipophilic food components. Adv Colloid Interface Sci. Sep. 15, 2010;159(2):213-28. doi: 10.1016/j.cis.2010.06.010. Epub Jul. 3, 2010.
Miller et al., Design of Functional Materials based on Liquid Crystalline Droplets. Chem Mater. Jan. 14, 2014;26(1):496-506. doi: 10.1021/cm4025028. Author manuscript provided. 26 pages.
Miniewicz et al., Photochromic and nonlinear optical properties of azo-functionalized POSS nanoparticles dispersed in nematic liquid crystals. Journal of Materials C. 2014;2:432-40. Epub Oct. 30, 2013.
Mondiot et al., Liquid crystal-based emulsions for synthesis of spherical and non-spherical particles with chemical patches. J Am Chem Soc. Jul. 10, 2013;135(27):9972-5. doi: 10.1021/ja4022182. Epub Apr. 19, 2013. Author manuscript provided. 10 pages.
Mukerjee et al., Adsorption of fluorocarbon and hydrocarbon surfactants to air-water, hexane-water and perfluorohexane-water interfaces. Relative affinities and fluorocarbon-hydrocarbon nonideality effects. J. Phys. Chem., 1981, 85(15): 2298-2303.
Nagelberg et al., Reconfigurable and responsive droplet-based compound micro-lenses. Nat Commun. Mar. 7, 2017;8:14673. doi: 10.1038/ncomms14673. Epub Mar. 7, 2017. 9 pages.
Nie et al., Janus and ternary particles generated by microfluidic synthesis: design, synthesis, and self-assembly. J Am Chem Soc. Jul. 26, 2006;128(29):9408-12.
Nisisako et al., Synthesis of monodisperse bicolored Janus particles with electrical anisotropy using a microfluidic co-flow system. Adv Mater. 2006;18:1152-6.
Niu et al., Optical biosensor based on liquid crystal droplets for detection of cholic acid. Optics Commun. 2016;381:286-91.
Ohm et al., A continuous flow synthesis of micrometer-sized actuators from liquid crystalline elastomers. Adv Mater. Dec. 18, 2009;21(47):4859-62. doi: 10.1002/adma.200901522.
Patravale et al., Novel cosmetic delivery systems: an application update. Int J Cosmet Sci. Feb. 2008;30(1):19-33. doi: 10.1111/j.1468-2494.2008.00416.x.
Perro et al., Design and synthesis of Janus micro- and nanoparticles. J Mater Chem. 2005;15:3745-60. Epub Jul. 25, 2005.
Riess, Overview of progress in the fluorocarbon approach to in vivo oxygen delivery. Biomater Artif Cells Immobilization Biotechnol. 1992;20(2-4):183-202.
Roh et al., Biphasic Janus particles with nanoscale anisotropy. Nat Mater. Oct. 2005;4:759-63. Epub Sep. 25, 2005.
Schutt et al., Injectable microbubbles as contrast agents for diagnostic ultrasound imaging: the key role of perfluorochemicals. Angew Chem Int Ed Engl. Jul. 21, 2003;42(28):3218-35.
Schwartz et al., Cholesteric Liquid Crystal Shells as Enabling Material for Information-Rich Design and Architecture. Adv Mater. Jul. 2018;30(30):e1707382. doi: 10.1002/adma.201707382. Epub May 14, 2018. 19 pages.
Shah et al., Designer emulsions using microfluidics. Materials Today, 2011; 11: 18-27.
Shah et al., Janus Supraparticles by Induced Phase Separation of Nanoparticles in Droplets. Adv. Mater. 2009; 21: 1949-1953. doi:10.1002/adma.200803115.
Shum et al., Droplet microfluidics for fabrication of non-spherical particles. Macromol Rapid Commun. Jan. 18, 2010;31(2):108-18. doi: 10.1002/marc.200900590. Epub Nov. 24, 2009.
Sivakumar et al., Liquid Crystal Emulsions as the Basis of Biological Sensors for the Optical Detection of Bacteria and Viruses. Advanced Functional Materials. 2009;19(14):2260-5. Epub Jul. 16, 2009.
Skarabot et al., Hierarchical self-assembly of nematic colloidal superstructures. Phys Rev E. Jun. 2008;77(6 Pt 1):061706. doi: 10.1103/PhysRevE.77.061706. Epub Jun. 12, 2008. 4 pages.
Song et al., Monodisperse w/w/w/ double emulsion induced by phase separation. Langmuir. 2012;28:12054-12059.
Tanaka et al., Dual stimuli-responsive "mushroom-like" Janus polymer particles as particulate surfactants. Langmuir. Jul. 20, 2010;26(14):11732-6. doi: 10.1021/la101237c.
Tschierske, Development of structural complexity by liquid-crystal self-assembly. Angew Chem Int Ed Engl. Aug. 19, 2013;52(34):8828-78. doi: 10.1002/anie.201300872. Epub Aug. 9, 2013.
Tu et al., One-step encapsulation and triggered release based on Janus particle-stabilized multiple emulsions. Chem Commun (Camb). Dec. 21, 2014;50(98):15549-52. doi: 10.1039/c4cc07854c. Epub Oct. 30, 2014.
Utada et al., Monodisperse double emulsions generated from a microcapillary device. Science. Apr. 22, 2005;308(5721):537-41.

(56) References Cited

OTHER PUBLICATIONS

Van Der Asdonk et al., Liquid crystal templating as an approach to spatially and temporally organise soft matter. Chem Soc Rev. Oct. 2, 2017;46(19):5935-5949. doi: 10.1039/c7cs00029d.

Walther et al., Janus particles. Soft Matter. 2008;4:663-8. Epub Feb. 26, 2008.

Wang et al., Liquid crystals: emerging materials for use in real-time detection applications. Journal of Materials Chemistry C. 2015;3:9038-47. Epub Aug. 4, 2015. Author manuscript provided. 23 pages.

Wang et al., Thermally reconfigurable Janus droplets with nematic liquid crystalline and isotropic perfluorocarbon oil compartments. Soft Matter. Mar. 20, 2019;15(12):2580-2590. doi: 10.1039/c8sm02600a. Author manuscript provided. 12 pages.

Wang et al., Topological defects in liquid crystals as templates for molecular self-assembly. Nat Mater. Jan. 2016;15(1):106-12. doi: 10.1038/nmat4421. Epub Sep. 21, 2015.

Wong et al., Bioinspired self-repairing slippery surfaces with pressure-stable omniphobicity. Nature. Sep. 21, 2011;477(7365):443-7. doi: 10.1038/nature10447.

Wu et al., Bioinspired nanocorals with decoupled cellular targeting and sensing functionality. Small. 2010;6(4):503-7.

Yang et al., Microfluidic synthesis of multifunctional Janus particles for biomedical applications. Lab Chip. Jun. 21, 2012;12(12):2097-102. doi: 10.1039/c2lc90046g. Epub May 14, 2012. Author manuscript provided. 14 pages.

Yi et al., Janus particles for biological imaging and sensing. Analyst. Jun. 21, 2016;141(12):3526-39. doi: 10.1039/c6an00325g. Epub Apr. 7, 2016. Author manuscript provided. 24 pages.

Yoshida et al., Structurally Controlled Bio-hybrid Materials Based on Unidirectional Association of Anisotropic Microparticles with Human Endothelial Cells. Adv Mater. Dec. 2009;21:4920-5.

Yuet et al., Multifunctional Superparamagnetic Janus Particles. Langmuir. Mar. 16, 2010;26(6):4281-7. doi:10.1021/la903348s. Epub Oct. 20, 2009.

Yusa et al., Fluorescence Studies of pH-Responsive Unimolecular Micelles Formed from Amphiphilic Polysulfonates Possessing Long-Chain Alkyl Carboxyl Pendants. Macromolecules. 2002; 35(27): 10182-88. doi: 10.1021/ma0212947. Epub Nov. 27, 2002.

Zarzar et al., Dynamically reconfigurable complex emulsions via tunable interfacial tensions. Nature. Feb. 26, 2015;518(7540):520-4. doi: 10.1038/nature14168. Author manuscript provided. 20 pages.

Zeininger et al., Rapid Detection of *Salmonella enterica* via Directional Emission from Carbohydrate-Functionalized Dynamic Double Emulsions. ACS Cent Sci. May 22, 2019; 5(5): 789-795. Epub Apr. 23, 2019.

Zeininger et al., Waveguide-based chemo- and biosensors: complex emulsions for the detection of caffeine and proteins. Lab on a Chip. 2019;19:1327-31. Epub Mar. 21, 2019.

Zhang et al., Emulsion Agglutination Assay for the Detection of Protein-Protein Interactions: An Optical Sensor for Zika Virus. ACS Sens. Jan. 25, 2019;4(1):180-184. doi: 10.1021/acssensors.8b01202. Epub Jan. 9, 2019. Author manuscript provided. 12 pages.

Zhang et al., Fabrication of Janus droplets by evaporation driven liquid-liquid phase separation. Chemical Communications. 2016;52:5015-8. Epub Mar. 7, 2016.

Zhang et al., Interfacial bioconjugation on emulsion droplet for biosensors. Bioorg Med Chem. Oct. 15, 2018;26(19):5307-13. Author manuscript. 20 pages.

Zhang et al., Janus emulsions for the detection of bacteria. ACS Central Sci. Apr. 26, 2017;3(4):309-13.

Zhang et al., Janus Particle Synthesis, Assembly, and Application. Langmuir. 2017;33(28):6964-77. Epub Jul. 5, 2017.

Zhang et al., Toward Design Rules of Directional Janus Colloidal Assembly. Ann Rev Phys Chem. 2015;66:581-600. doi: 10.1146/annurev-physchem-040214-121241. Epub Feb. 4, 2015.

Zhang et al., Ultra-small droplet generation via volatile component evaporation. Lab Chip. Apr. 21, 2014;14(8):1395-400. doi: 10.1039/c3lc51183a.

Zhao et al., Microfluidic mass-transfer control for the simple formation of complex multiple emulsions. Angew Chem Int Ed. 2009;48:7208-11.

Claessens et al., Highly Efficient Synthesis of Chloro- and Phenoxy-Substituted Subphthalocyanines. Jun. 26, 2003;2003(14):2547-51.

Ong et al., Dynamic self-correcting nucleophilic aromatic substitution. Nat Chem. Sep. 3, 2018;10:1023-30.

Wang et al., Janus magneto-electric nanosphere dimers exhibiting unidirectional visible light scattering and strong electromagnetic field enhancement. ACS Nano. Jan. 27, 2015;9(1):436-48. doi: 10.1021/nn505606x. Epub Jan. 6, 2015.

U.S. Appl. No. 16/695,647, filed Nov. 26, 2019, Swager et al.

U.S. Appl. No. 17/001,401, filed Aug. 24, 2020, Swager et al.

\* cited by examiner

SYSTEMS INCLUDING JANUS DROPLETS WITH BINDING MOIETIES FOR A VIRUS, A PATHOGEN OR A BACTERIUM

CROSS REFERENCE TO RELATED APPLICATIONS

This Application is a Continuation of U.S. application Ser. No. 16/202,007, filed Nov. 27, 2018, entitled "SYSTEMS INCLUDING JANUS DROPLETS,", which is a Continuation-in-part of U.S. application Ser. No. 16/113,520 filed Aug. 27, 2018, entitled "SYSTEMS INCLUDING JANUS DROPLETS", now abandoned, which is a Continuation of U.S. application Ser. No. 15/269,543, filed Sep. 19, 2016, entitled "SYSTEMS INCLUDING JANUS DROPLETS," issued as U.S. Pat. No. 10,060,913, each of which is incorporated herein by reference in their entirety.

STATEMENT OF GOVERNMENT SUPPORT

This invention was made with Government support under Grant No. R01-GM095843 awarded by the National Institutes of Health. The Government has certain rights in the invention.

FIELD OF THE INVENTION

The present invention generally relates to systems and methods including Janus droplets.

BACKGROUND

Emulsification is a powerful age-old technique for mixing and dispersing immiscible components within a continuous liquid phase. Consequently, emulsions are central components of medicine, food, and performance materials. Complex emulsions, including multiple emulsions and Janus droplets, are of increasing importance in pharmaceuticals and medical diagnostics, in the fabrication of microdroplets and capsules for food, in chemical separations, for cosmetics, for dynamic optics, and chemical separations. However, quantitative detections of analytes with high sensitivity and selectivity using Janus droplets have yet to be realized. Accordingly, improved systems and methods are needed.

SUMMARY OF THE INVENTION

The present invention provides systems and methods including Janus droplets.

In one aspect, systems are provided. In some embodiments, the system comprises a plurality of Janus droplets associated with binding moieties to an analyte, the binding moiety and analyte selected such that when the analyte binds to the binding moiety at least a portion of the plurality of Janus droplets are changed in orientation sufficient to change electromagnetic radiation interacting with the plurality of Janus droplets in a detectable manner.

In some embodiments, the system comprises a plurality of Janus droplets associated with a plurality of binding moieties to an analyte and a detector positioned relative to the plurality of Janus droplets such that when sufficient numbers of the binding moieties bind to analyte at least a portion of the plurality of Janus droplets are changed in orientation sufficient to change electromagnetic radiation interacting with the Janus droplets in a manner determinable by the detector.

In certain embodiments, upon binding to the binding moieties, at least a portion of the plurality of Janus droplets agglutinate.

In certain embodiments, prior to binding to the binding moieties, the plurality of Janus droplets are oriented such that at least a portion of interfaces between a first phase and a second phase within each Janus droplet are aligned parallel with respect to one another.

In certain embodiments, prior to the analyte binding to the binding moieties, the plurality of Janus droplets are bound to a surface.

In certain embodiments, upon binding of the analyte to the binding moieties, at least a portion of the plurality of Janus droplets unbind from the surface.

In certain embodiments, the system comprises a source of external energy applicable to the composition to generate a determinable signal and a detector positioned to detect the signal.

In certain embodiments, the signal comprises electromagnetic radiation.

In certain embodiments, upon exposure of the article to a chemical or biological analyte, the system generates the determinable signal.

In another aspect, methods are provided. In some embodiments, the method comprises allowing an analyte to bind to binding moieties associated with a plurality of Janus droplets and determining a change in electromagnetic radiation interacting with the plurality of Janus droplets due at least in part to the binding of the analyte to the binding moieties.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby producing a detectable change in an optical property of the article and determining the detectable change.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby changing the optical transmission of the article.

In certain embodiments, the plurality of Janus droplets comprise one or more amphiphilic compounds including at least one binding moiety.

In certain embodiments, interacting with at least a portion of the article comprises binding of the chemical or biological analyte to the at least one binding moiety.

In certain embodiments, prior to exposing the article to a chemical or biological analyte, at least a portion of the plurality of Janus droplets are oriented such that at least a portion of interfaces between a first phase and a second phase within each Janus droplet are aligned parallel with respect to one another.

In certain embodiments, substantially all of the interfaces between a first phase and a second phase within each Janus droplet are aligned parallel with respect to one another.

In certain embodiments, upon exposing the article to a chemical or biological analyte, at least a portion of the plurality of Janus droplets agglutinate.

In certain embodiments, upon exposing the article to a chemical or biological analyte, at least a portion of the plurality of Janus droplets are oriented such that at least a portion of interfaces between a first phase and a second phase within each Janus droplet are not aligned parallel with respect to one another.

In certain embodiments, at least a portion of the plurality of Janus droplets are bound to a surface of the article via the binding moiety.

In certain embodiments, upon exposing the article to a chemical or biological analyte, at least a portion of the plurality of Janus droplets unbind from the surface.

In yet another aspect, articles are provided. In some embodiments, the article comprises an outer phase and a plurality of Janus droplets dispersed within the outer phase, wherein at least a portion of the plurality of Janus droplets comprise an amphiphilic compound including at least one binding moiety.

In certain embodiments, the plurality of Janus droplets is oriented such that at least a portion of interfaces between a first phase and a second phase within each Janus droplet are aligned parallel with respect to one another.

In certain embodiments, the at least one binding moiety is capable of binding with a chemical or biological analyte.

In certain embodiments, upon binding of the at least one binding moiety with a chemical or biological analyte, at least a portion of the plurality of Janus droplets change orientation.

In certain embodiments, the plurality of Janus droplets are substantively transmissive to electromagnetic radiation.

In certain embodiments, upon binding of the at least one binding moiety with a chemical or biological analyte, the plurality of Janus droplets decrease in optical transmission.

In some embodiments, the article comprises a surface, an outer phase deposited on at least a portion of the surface, and a plurality of Janus droplets dispersed within the outer phase, wherein at least a portion of the plurality of Janus droplets comprise an amphiphilic compound including at least one binding moiety, and wherein at least a portion of the plurality of Janus droplets are bound to the surface via the binding moiety.

In certain embodiments, at least a portion of the plurality of Janus droplets are oriented such that an interface between a first phase and a second phase within each Janus droplet are not aligned parallel to the surface.

In certain embodiments, upon exposure of the plurality of Janus droplets to a biological or chemical analyte, at least a portion of Janus droplets unbind from the surface.

In certain embodiments, upon exposure of the plurality of Janus droplets to a biological or chemical analyte, at least a portion of Janus droplets change orientation.

In certain embodiments, the article is substantively visible-light transmissive after exposure to the plurality of Janus droplets to the biological or chemical analyte.

In certain embodiments, upon exposure of the plurality of Janus droplets to a chemical or biological analyte, the plurality of Janus droplets increase in optical transmission.

In certain embodiments, each Janus droplet comprises a first phase and a second phase, immiscible with the first phase.

In certain embodiments, the outer phase is an aqueous phase.

In certain embodiments, the first phase comprises a hydrocarbon, a fluorocarbon, a silicone, a liquid crystal, an ionic liquid, a polymer, combinations thereof, or derivatives thereof.

In certain embodiments, the second phase comprises a hydrocarbon, a fluorocarbon, a silicone, a liquid crystal, an ionic liquid, a polymer, combinations thereof, or derivatives thereof, immiscible with the first phase.

In certain embodiments, the amphiphilic compound is selected from the group consisting of: ionic surfactants, non-ionic surfactants, zwitterionic surfactants, polymers, proteins, DNA, RNA, acids, carbohydrates, saccharides, enzymes, chromophores, lipids, graphene oxide, combinations thereof, and derivatives thereof.

In an exemplary embodiment, the surface is gallic acid.

In another exemplary embodiment, the surfactant is maleimide-functionalized polystyrene-b-polyacrylic acid.

In certain embodiments, an interface between the outer phase and the plurality of Janus droplets comprises the amphiphilic compound.

In certain embodiments, the analyte comprises a biological compound, a drug, a macromolecule, a salt, an electrolyte, an enzyme, an acid, a nucleic acid, a carbohydrate, a peptide, a protein, a phosphate, a sulfonate, a virus, a pathogen, an oxidant, a reductant, a toxin, a chemical warfare agent, an explosive, carbon dioxide, or combinations thereof.

In certain embodiments, the analyte is a single analyte.

In certain embodiments, the analyte is a virus. In some embodiments, the virus is a zika virus.

In some embodiments, the system comprises a plurality of Janus droplets associated with a plurality of binding moieties to a virus and a detector positioned relative to the plurality of Janus droplets such that when sufficient numbers of the binding moieties bind to the virus at least a portion of the plurality of Janus droplets are changed in orientation sufficient to change electromagnetic radiation interacting with the Janus droplets in a manner determinable by the detector.

In some embodiments, the method comprises exposing, to an article comprising an outer phase and a plurality of Janus droplets dispersed within the outer phase, a sample suspected of containing a virus, wherein the virus, if present, interacts with at least a portion of the article such that at least a portion of the plurality of Janus droplets change orientation thereby producing a detectable change in an optical property of the article and determining the detectable change.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

(FIG. 10A) Synthesis of maleimide functionalized surfactant P1-MA from a polystyrene-b-polyacrylic acid polymer. (FIG. 10B) Bioconjugation of rcSso7d to the droplet H/W interface via maleimide-thiol chemistry.

(FIG. 12A) Experimental setup with both excitation and detection source from the top of the emulsion layer. (FIG. 12B) Scheme showing the backscattering of the light with naturally oriented Janus droplets and agglutinated droplets. (FIG. 12C) Optical measurement with the intensity ratio $I_{exc}/I_H$ in correlation to the streptavidin concentration.

(FIG. 13A) Experimental setup with the optical fiber at the bottom of the emulsion layer. (FIG. 13B) Scheme showing the mechanism of the attenuated emission of the perylene dye may depend, in some cases, on the orientation of the droplets. (FIG. 13C) Experimental data showing the optical detection of the emission intensity ration $I_H/I_F$ in correlation of the streptavidin concentration.

Figure 1A:
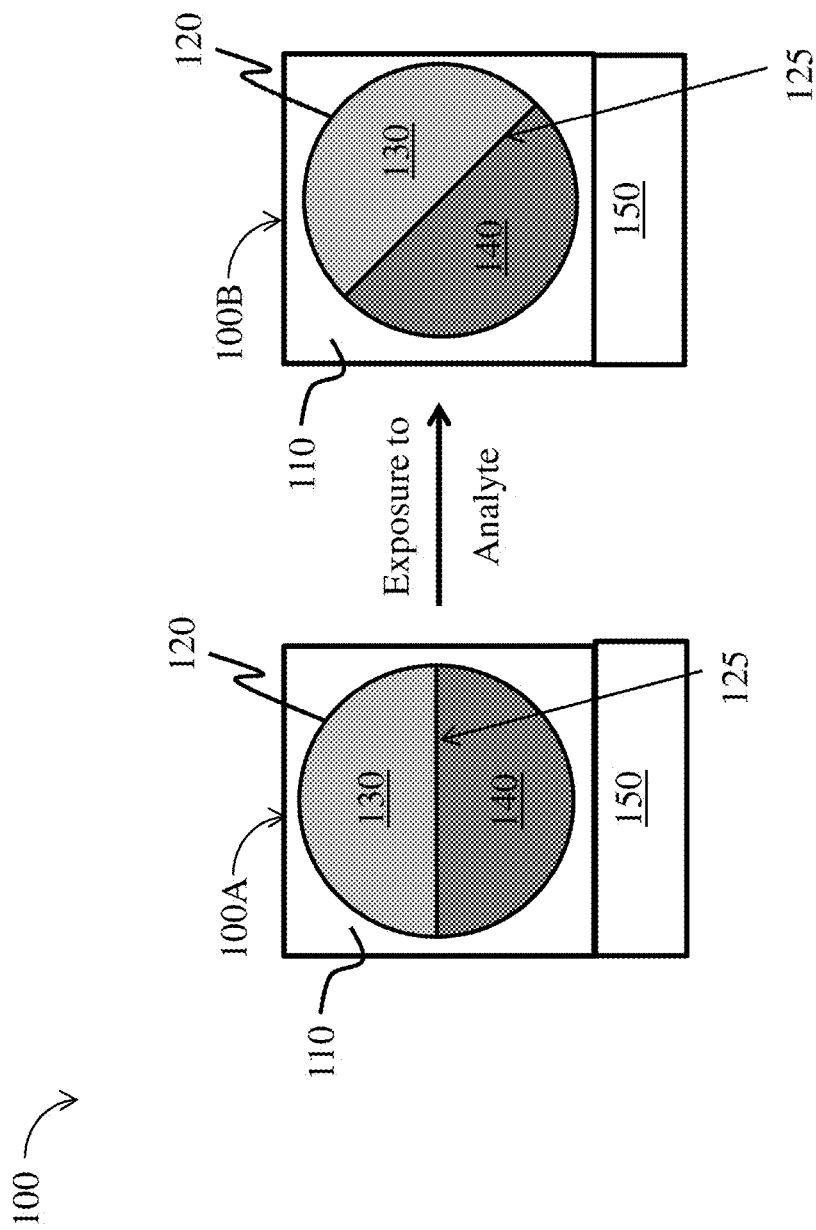
FIG. 1A illustrates a system including a Janus droplet, exposed to an analyte, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful in the detection of analytes. The systems and methods may allow for a relatively simple and rapid way for detecting analytes such as chemical and/or biological analytes and may be useful in numerous applications including sensing, food manufacturing, medical diagnostics, performance materials, dynamic lenses, water monitoring, environmental monitoring, detection of proteins, detection of DNA, among other applications. For example, the systems and methods described herein may be used for determining the presence of a contaminant such as bacteria (e.g., detecting pathogenic bacteria in food and water samples which helps to prevent widespread infection, illness, and even death). Advantageously, the systems and methods described herein may not have the drawbacks in current detection technologies including, for example, relatively high costs, long enrichment steps and analysis times, and/or the need for extensive user training. Another advantageous feature provided by the systems and methods described herein includes fabrication in a relatively large scale. In some embodiments, the systems and methods may be used in conjunction with a detector including handheld detectors incorporated with, for example, smartphones (e.g., for the on-site detection of analytes such as pathogenic bacteria). For example, such systems could be used by the food industry to prevent extensive foodborne illnesses which may result in expensive medical treatment costs, lawsuits, government sanctions, product recalls, and/or tarnished long-term reputations. Articles comprising Janus droplets are also provided.

In some embodiments, the systems and methods comprise a plurality of Janus droplets. Janus droplets generally include two or more phases immiscible with one another and/or having distinct physical and/or chemical properties, within the droplet. In certain embodiments, when equal amounts of the two immiscible phases are present and the interfactial tensions are properly balanced, the Janus droplets will be spherical with each hemisphere of the sphere comprising one of the immiscible phases. In certain embodiments, the plurality of Janus droplets includes a first phase and a second phase immiscible with the first phase. In some embodiments, the plurality of Janus droplets may be dispersed within an outer phase (e.g., an aqueous phase). For example, in some embodiments, the system comprises an aqueous phase and a plurality of Janus droplets comprising a hydrocarbon and a fluorocarbon. In some cases, the plurality of Janus droplets may be associated a binding moiety (e.g., a binding moiety associated with the Janus droplets and/or a binding moiety present on a surfactant incorporated with the plurality of Janus droplets). In some embodiments, the binding moiety may bind with an analyte (e.g., a biological and/or chemical analyte) such that the orientation of at least a portion of the plurality of Janus droplets is changed. The change in orientation of a Janus droplet may result in a change in the interaction of electromagnetic radiation (e.g., visible light) with the Janus droplet in a detectable manner. In some embodiments, exposing a plurality of Janus droplets to an analyte causes a detectable change in an optical property of the Janus droplets, such that the analyte can be determined and/or quantified.

In certain embodiments, upon exposure to an analyte, at least a portion of the plurality of Janus droplets may agglutinate. For example, in some cases, the analyte may facilitate the agglutination of at least a portion of the plurality of Janus droplets. The agglutination of some Janus droplets may result in a detectable change in the interaction of electromagnetic radiation (e.g., visible light) with the Janus droplets. In some cases, the agglutination of some Janus droplets may result in a change in orientation of each of the Janus droplets (e.g., relative to the orientation of the Janus droplets prior to exposure to the analyte). In other cases, the Janus droplets may be in a agglutinated state prior to exposure to an analyte and the exposure of the system to the analyte will disrupt agglutination and case a change in the orientation of the Janus droplet.

Advantageously, in some embodiments, the systems described herein may enable highly sensitive detection of analytes including, for example, detection of single analyte interaction events (e.g., binding events, chemical reactions, biological reactions). In an illustrative embodiment, a single analyte (e.g., one protein, one strand of DNA, one strand of RNA) may cause the agglutination of some Janus droplets and changing the orientation of each of the agglutinated Janus droplets, such that a single analyte (e.g., a single protein, a single strand of DNA, RNA etc.) is detected. In some such embodiments, the single analyte may bind to some Janus droplets such that the Janus droplets agglutinate. In another illustrative embodiment, a single analyte may cause the orientation of a single Janus droplet to change (e.g., via enzymatic degradation of a tether bound to the Janus droplet), such that a single analyte is detected. In some embodiments, a plurality of analytes and/or types of analytes may be detected (e.g., via the change in orientation of a plurality of Janus droplets and/or the agglutination of groups of Janus droplets). In certain embodiments, the concentration of an analyte exposed to the system may be determined by measuring the number of Janus droplets changing orientation upon exposure of the system to the analyte.

As illustrated in FIG. 1A, in some embodiments, system 100 comprises a plurality of Janus droplets such as Janus droplet 120. In certain embodiments, Janus droplet 120 comprises first phase 130 (e.g., comprising a hydrocarbon) and second phase 140 (e.g., comprising a fluorocarbon). As depicted illustratively in FIG. 1A, in some embodiments, first phase 130 and second phase 140 may have relatively the same volume in each Janus droplet. However, those skilled in the art would understand based upon the teaching of this specification that the volume of the first phase and the second phase may not be equal.

In some embodiments, as depicted in FIG. 1A, Janus droplet 120 has a particular orientation, such as orientation 100A. The orientation of a Janus droplet as described herein may be determined by measuring the angle of a planar surface defined by the interface (e.g., interface 125) between the first phase (e.g., first phase 130) and the second phase (e.g., second phase 140). In some embodiments, upon exposure of Janus droplet 120 to an analyte, the Janus droplet may change orientation (e.g., from orientation 100A to orientation 100B). In some such embodiments, the analyte may bind with a binding moiety present on the Janus droplet, resulting in the change in orientation of the Janus droplet. As illustrated in FIG. 1A, the orientation of interface 125 in orientation 100B is different than the orientation of interface 125 in orientation 100A. For example, in some embodiments, the Janus droplet may rotate upon exposure to the analyte (e.g., upon binding of the analyte with a binding moiety associated with the Janus droplet). In some embodiments, the change in orientation of the Janus droplet is determinable (e.g., measurable) such that it indicates the presence of an analyte.

The Janus droplets described herein may be useful in a number of applications. In an exemplary embodiment, the Janus droplets described herein may be used for sensing of an analyte. For example, in some such embodiments, the Janus droplets may change orientation upon exposure to an analyte such that the change in orientation can be detected (e.g., by a change in optical transmission, polarization, birefringence, etc. of the colloid). In another exemplary embodiment, the Janus droplets described herein may be used as tunable lenses. In certain embodiments, measurements of the optical properties (e.g., transmission, absorption, reflection, focal distance, and scattering) of the Janus droplets can be indicative of specific droplet orientations. For example, when a change in droplet orientation is correlated with an analyte of interest (i.e., enzyme, pollutant, virus, bacteria, DNA, RNA, etc.), then, the Janus droplets can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the Janus droplets over time can be used to, for example, analyze reaction rates or analyte concentrations. In some such embodiments, the orientation of the Janus droplets changes in the presence of an analyte such that the system obtains a transparent state over a particular range of time, or alternatively, obtains a relatively opaque state over a particular range of time.

Those skilled in the art would understand that changing a property of a Janus droplet refers to a property of the Janus droplet immediately before that differs in a substantially measurable way from the property of the Janus droplet at some relatively short time (e.g., seconds, minutes, hours) after exposure to the analyte. Those skilled in the art would also be capable of selecting methods for determining the change in the property of the Janus droplets (e.g., measuring the average birefringence, measuring the optical transmission at one or more wavelength, measuring the density, etc.) based upon the specification and examples below.

Figure 1B:
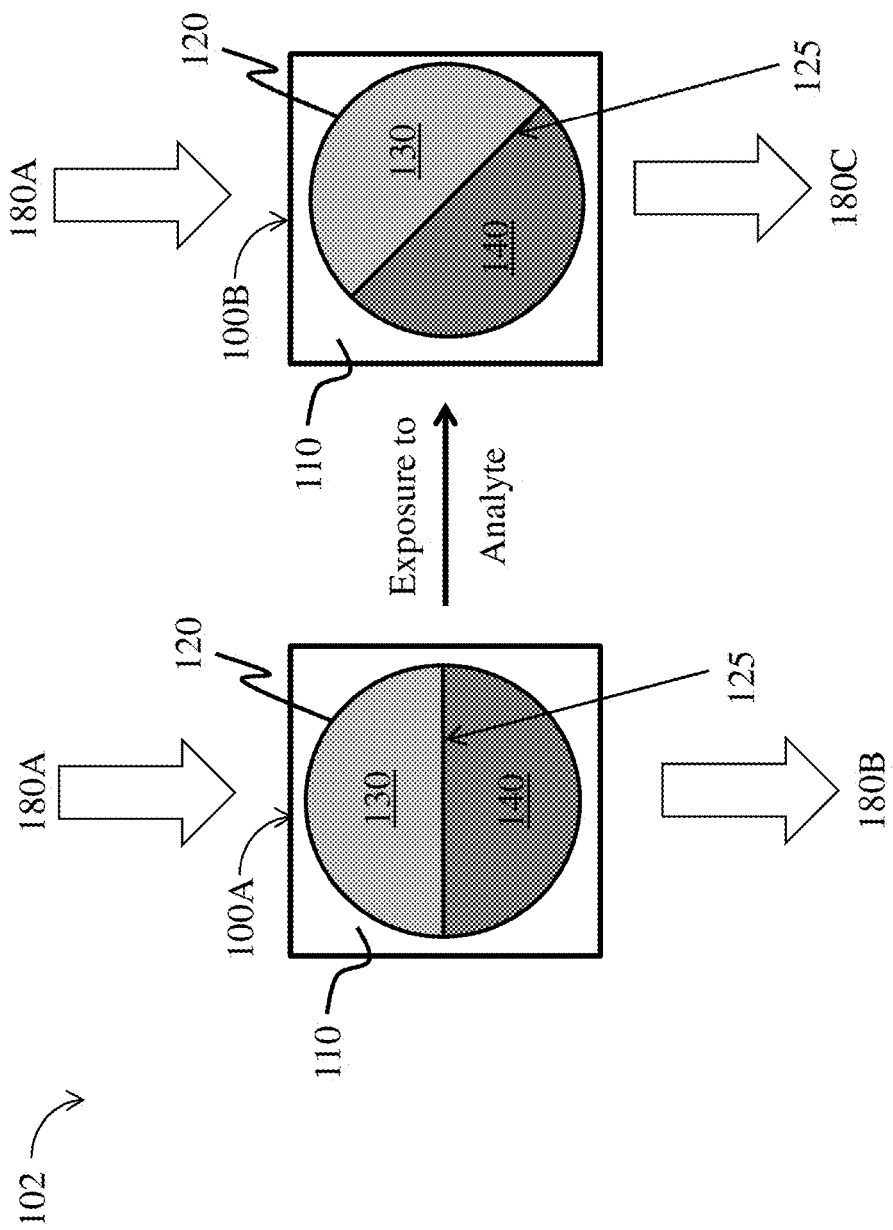
FIG. 1B illustrates a system including a Janus droplet, exposed to an analyte, according to one set of embodiments.

For example, as illustrated in FIG. 1B, system 102 comprises a plurality of Janus droplets such as exemplary Janus droplet 120. In some embodiments, electromagnetic radiation 180A interacts with Janus droplet 120. In certain embodiments, upon exposure of system 102 to an analyte (e.g., such that the analyte binds to a binding moiety associated with the Janus droplet), Janus droplet 120 changes orientation (e.g., from orientation 100A to 100B) sufficiently to change the interaction of electromagnetic radiation 180A with the Janus droplets as compared to the interaction of electromagnetic radiation 180A prior to exposure to the analyte. For example, prior to exposure to the analyte, Janus droplet 120 may interact with electromagnetic radiation 180A such that electromagnetic radiation 180B is produced. In some embodiments, electromagnetic radiation 180A and electromagnetic radiation 180B may be substantially the same. For example, Janus droplet 120 may have an orientation 100A such that electromagnetic radiation interacting with (e.g., transmitting perpendicular to interface 125 of Janus droplet 120) is not substantially changed in wavelength and/or amplitude.

For example, in some cases, the plurality of Janus droplets may be orientation such that the system is substantially optically transparent in a direction perpendicular to the surface of the interface between the first phase and the second phase (e.g., interface 125). In some cases, however, electromagnetic radiation 180B may be different than electromagnetic radiation 180A in wavelength and/or amplitude. In some embodiments, upon exposure of system 102 to an analyte, Janus droplet 120 changes orientation from orientation 100A to orientation 100B, such that electromagnetic radiation 180A interacts with Janus droplet 120 and produced electromagnetic radiation 180C, different than electromagnetic radiation 180B.

In some embodiments, the plurality of Janus droplets is changed in orientation (e.g., upon exposure to an analyte) sufficient to change electromagnetic radiation interacting with the plurality of Janus droplets in a detectable manner. In certain embodiments, at least a portion of the Janus droplets change orientation thereby changing the optical transmission of the article and/or thereby producing a detectable change in an optical property of the article. In some embodiments, the detectable change includes a change in color, average luminescence in one or more directions, and/or average optical transmission of the Janus droplet (or system comprising the plurality of Janus droplets).

In some embodiments the electromagnetic radiation (e.g., the electromagnetic radiation prior to interacting with the Janus droplet, the electromagnetic radiation after interacting with the Janus droplet) may comprise any suitable wavelength, including but not limited to infrared light (e.g., a wavelength between about 700 nm and about 1 cm), to visible light (e.g., a wavelength between about 400 nm and about 700 nm), and to ultraviolet (UV) light (e.g., a wavelength between about 10 nm and about 400 nm).

Figure 1C:
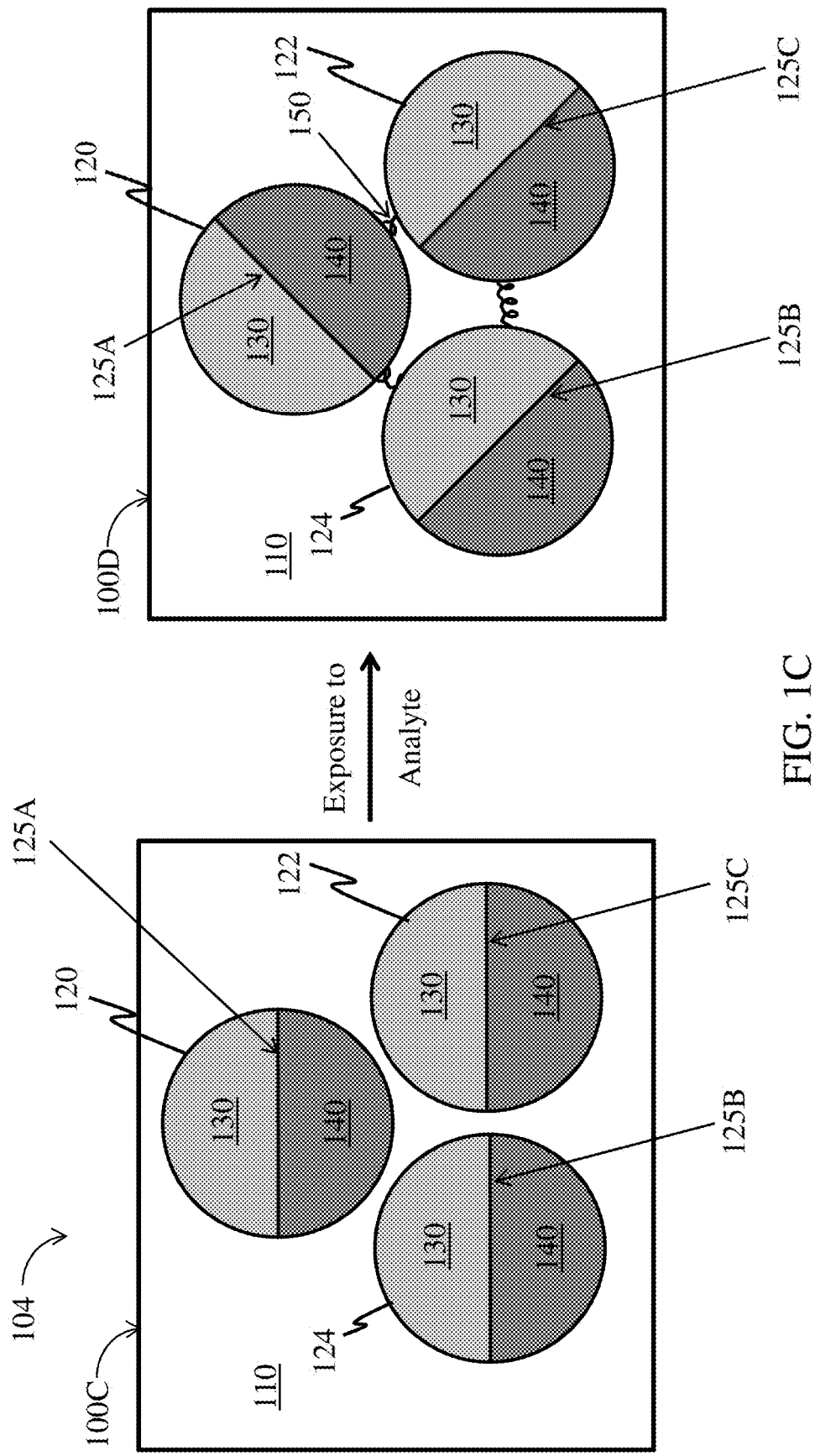
FIG. 1C illustrates a system including a plurality of Janus droplets, exposed to an analyte, according to one set of embodiments.

In certain embodiments, the plurality of Janus droplets (e.g., Janus droplets 120) is dispersed within an outer phase 110, as illustrated in FIGS. 1A-1C. In some embodiments, the outer phase is an aqueous phase (e.g., comprising water). The aqueous phase may also comprise, in some cases, solutes including organic molecules, proteins, ions, cells, DNA, RNA, cell lysates, or biological organisms. In some embodiments, exposing the system to the analyte comprises introducing the analyte into the outer phase. In certain embodiments, the analyte may be added to the outer phase such that the plurality of Janus droplets is exposed to the analyte.

In certain embodiments, the plurality of Janus droplets may be adjacent a surface 150, as illustrated in FIG. 1A. As used herein, when a component (e.g., a Janus droplet) is referred to as being "adjacent" another component (e.g., a surface), it can be directly adjacent to the component, or an intervening component (e.g., a fluid) also may be present. A component that is "directly adjacent" another component means that no intervening component is present (e.g., the component and another component are in contact with one another). Surface 150 may comprise a reflective surface such that exposing the system to an analyte causes a detectable change in an optical property of the Janus droplets such that the reflected electromagnetic radiation from surface 150 is also changed. In an exemplary embodiment, the plurality of Janus droplets is substantially transparent such that surface 150 is visible (e.g., when viewed perpendicular to surface 150) and, upon exposure to an analyte, the plurality of Janus droplets decrease in optical transmission such that at least a portion of surface 150 is obscured. Surface 150 may, in some cases, also be transparent such that light is transmitted through the surface and Janus droplets, such that exposure to an analyte will change the transmission of the light.

In some embodiments, at least a portion of the plurality of Janus droplets are orientated parallel (e.g., as measuring by the angle of a planar surface defined by the interface between the first phase and the second phase of the Janus droplet) to the surface. For example, referring again to FIG. 1A, in some embodiments, interface 125 of Janus droplet 120 (prior to exposure to an analyte) is orientated substantially parallel to surface 150 adjacent Janus droplet 120. In certain embodiments, the plurality of Janus droplets may be orientated substantially parallel to one another (e.g., substantially aligned). In some embodiments, prior to exposure to an analyte, the plurality of Janus droplets is aligned/oriented by the force of gravity (e.g., the first phase or the second phase having a greater density than the other phase) such that at least a portion of the plurality of Janus droplet are oriented substantially parallel with one another. In other embodiments, the forces that cause alignment of Janus droplets may include electrical or magnetic fields. For example, in certain embodiments, the plurality of Janus droplets may include a magnetic phase (e.g., including ferromagnetic particles)

In some embodiments, exposure to an analyte results in the agglutination of a plurality of Janus droplets. For example, as illustrated in FIG. 1C, system 104 comprises a plurality of Janus droplets (e.g., exemplary Janus droplets 120, 122, and 124). In certain embodiments, the plurality of Janus droplets may be orientated (relative to interfaces 125A, 125B, and 125C) substantially parallel to one another. In some embodiments, the interface between the first phase and the second phase of at least a portion the plurality of Janus droplet is aligned normal to the primary direction of the force of gravity such that the plurality of Janus droplets are oriented substantially parallel to one another. In some embodiments, upon exposure to an analyte, at least a portion of the Janus droplets agglutinate. In certain embodiments, agglutination of the Janus droplets results in a change of orientation of at least a portion of the Janus droplets (e.g., as measured by the change in angle of interfaces 125A, 125B, and 125C).

In certain embodiments, a binding moiety associated with the Janus droplet may bind with the analyte such that the Janus droplets agglutinate. For example, referring again to FIG. 1C, upon exposure to an analyte, the analyte may bind to a binding moiety on two or more Janus droplets (e.g., forming a bound complex 150 between two or more Janus droplets such as between Janus droplet 120 and Janus droplet 122). One of ordinary skill in the art would understand, based upon the teachings of this specification, that while bound complex 150 is illustrated as binding between first phase 130 and second phase 140, that formation of a bound complex between first phase 130 and first phase 130 of two droplets, is also possible. For example, as shown illustratively in FIG. 15, droplet 120 and droplet 122 are agglutinated via bound complex 152 between first phase 130 of droplet 120 and first phase 130 of droplet 122. Other configurations are also possible.

Figure 1D:
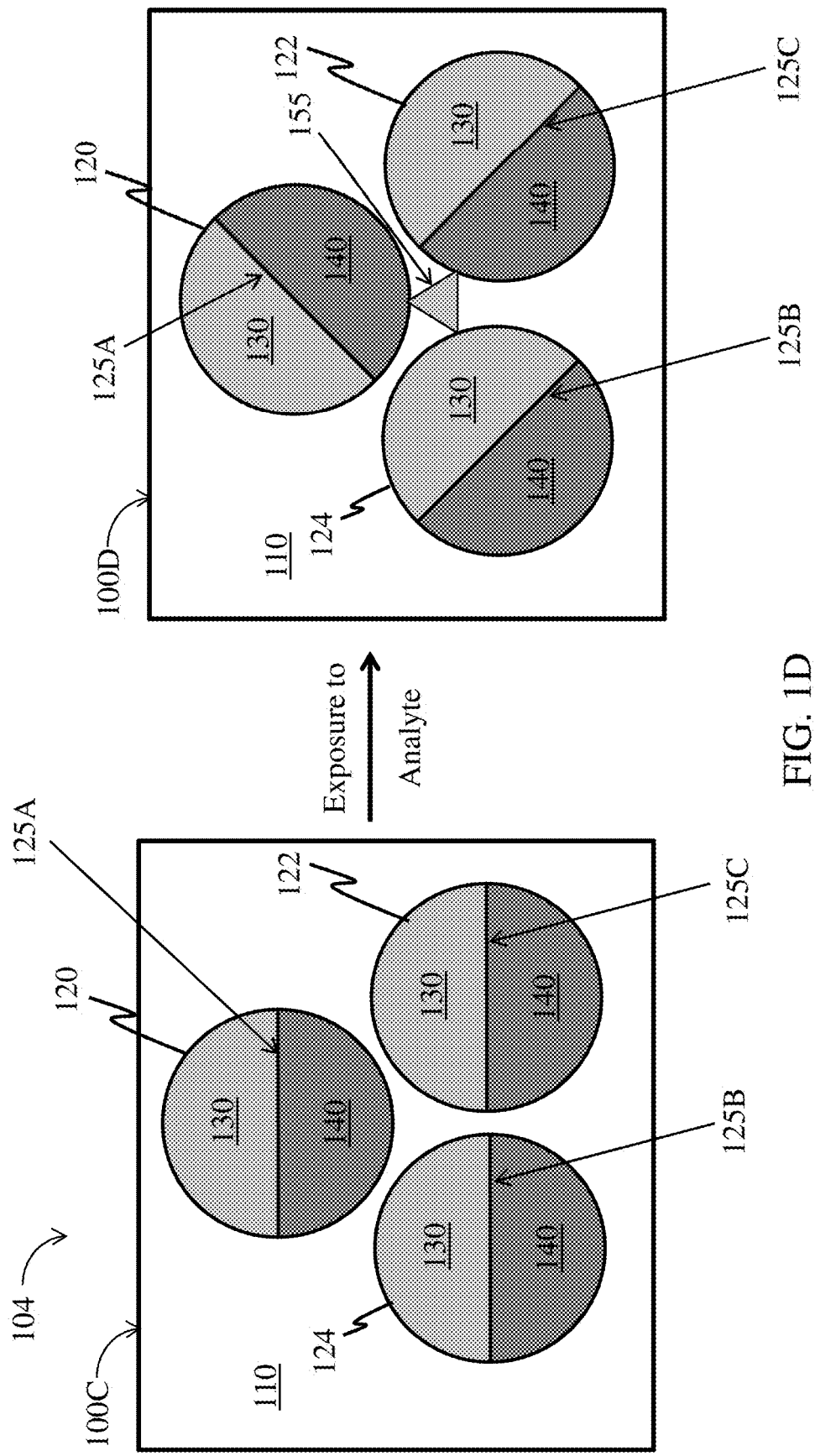
FIG. 1D illustrates a system including a plurality of Janus droplets, exposed to an analyte, according to one set of embodiments.

In some embodiments, a plurality of binding moieties (e.g., binding moieties associated with one or more Janus droplets) may bind with one or more analytes mutlivalently. For example, as illustrated in FIG. 1D, analyte 155 binds multivalently with Janus droplet 120, Janus droplet 122, and Janus droplet 124 such that the Janus droplets agglutinate. In some such embodiments, upon exposure and binding to the analyte, the Janus droplets change orientation sufficient to change electromagnetic radiation interacting with the plurality of Janus droplets in a detectable manner.

In some embodiments, upon agglutination of two or more Janus droplets, at least a portion of incident electromagnetic radiation may retroreflect amongst the droplets such that at least a portion of the electromagnetic radiation is reflected. For example, as shown illustratively in FIG. 15, system 106 comprises a plurality of Janus droplets (e.g., exemplary Janus droplets 120 and 122). In certain embodiments, the plurality of Janus droplets may be orientated (relative to interfaces 125A, and 125B) substantially parallel to one another (100C) and such that electromagnetic radiation 160 is transmitted through the interfaces. In some embodiments, upon exposure to an analyte, at least a portion of the Janus droplets agglutinate (100D). In certain embodiments, agglutination of the Janus droplets results in a change of orientation (100D) of at least a portion of the Janus droplets (e.g., as measured by the change in angle of interfaces 125A and 125B). In some embodiments, the Janus droplets change angle such that at least a portion of electromagnetic radiation 160 is reflected off of interfaces 125A and 125B. In some embodiments, at least a portion of electromagnetic radiation may still transmit through system 106. In some embodiments, the portion of electromagnetic radiation 160 that is reflected may be detected (e.g., by an optical detector, by a user) indicating the presence of the analyte (e.g., the analyte that results in agglutination of the Janus droplets) in the system.

Figure 2:
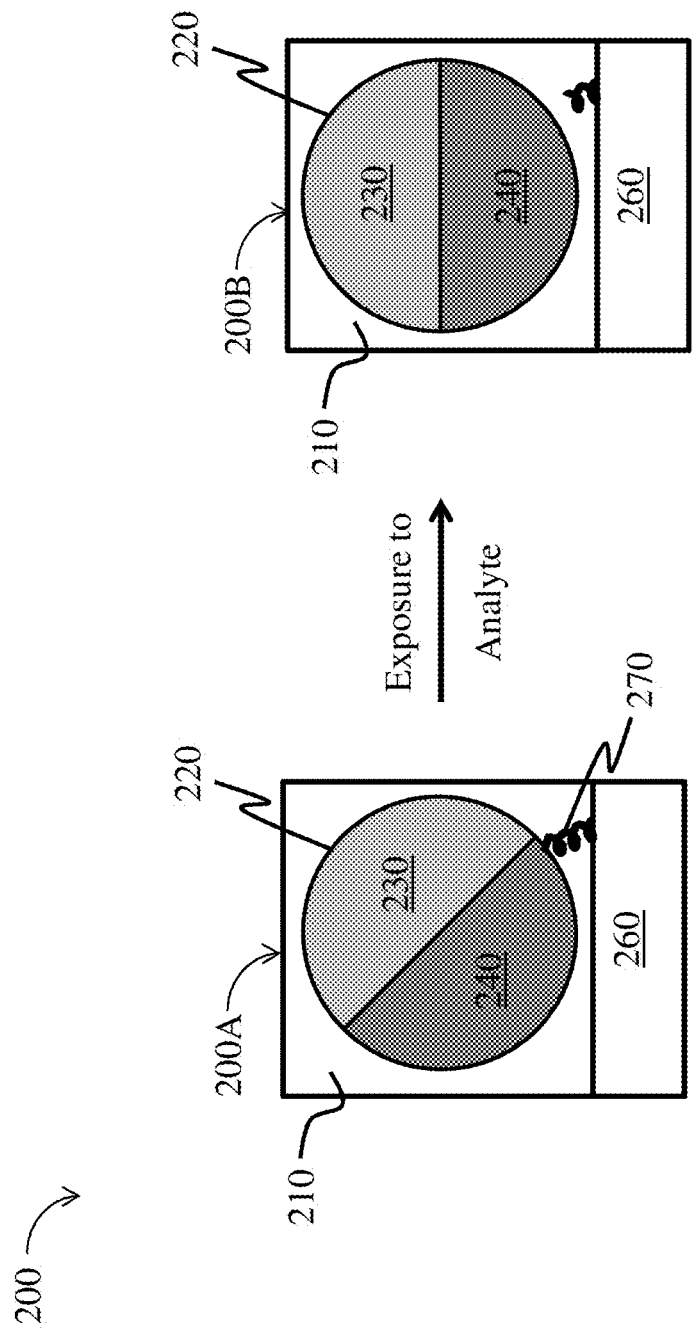
FIG. 2 illustrates a system including a Janus droplet, according to one set of embodiments.

In certain embodiments, the system may comprise a plurality of Janus droplets tethered (e.g., bound) to a surface. In some embodiments, exposure of the system to an analyte results in the breaking (e.g., cleavage) of the tether such that at least a portion of the Janus droplets change orientation (e.g., sufficient to change electromagnetic radiation interacting with the plurality of Janus droplets in a detectable manner). For example, as illustrated in FIG. 2, system 200 comprises Janus droplet 220 comprising first phase 230 and second phase 240, tethered to surface 260 adjacent Janus droplet 220 via tether 270. In some embodiments, exposure to an analyte results in the breaking of tether 270 such that Janus droplet 220 changes orientation (from orientation 200A prior to exposure to the analyte to orientation 200B upon exposure to the analyte). Those skilled in the art would understand based upon the teachings of this specification that surface 260 need not be planar and could be, for example, curved (e.g., the surface comprises a polymeric and/or inorganic particle). In some cases the surface may include an assembly of molecules such as proteins, DNA or RNA. In certain embodiments, the surface may comprise biological tissue (e.g., comprising skin (e.g., human skin), organ tissues, cells, or the like). In some cases, the surface may be a liquid immiscible with the outer phase and/or one or more phases present within the Janus droplets. In some embodiments, the surface comprises a polymeric material.

In some embodiments, the Janus droplet is tethered to the surface such that the interface between the first phase and the second phase is not parallel to the adjacent substrate and/or is not parallel with at least a portion of the plurality of Janus droplets. In some such embodiments, upon breaking of the tether by the analyte, at least a portion of the Janus droplets change orientation (e.g., such that at least a portion of the Janus droplets are parallel with one another and/or are parallel with an adjacent substrate). In some cases, breaking of the tether by the presence of an analyte resulting in an increase in the optical transmission of the system (e.g., such that a feature on the substrate is visible when viewed perpendicular to the surface). The tether may include, for example, one or more proteins, a polymer, one or more strands of DNA, one or more strands of RNA, or combinations thereof. Other tethers are also possible.

The analyte may break the tether in any suitable manner. For example, in some embodiments, the analyte may cleave the tether (e.g., via enzymatic degradation). In certain embodiments, the analyte may cleave the tether by changing the pH of the outer phase such that the tether breaks. In some embodiments, the analyte may cause the cleavage of the tether such that one or more binding moieties associated with (e.g., integrated within) the plurality of Janus droplets bind to the analyte. In some such embodiments, one or more binding moieties may be bound to the tether such that the Janus droplet is bound to the surface and, upon exposure to the analyte, the binding moiety unbinds from the tether and binds to the analyte.

In some cases, the binding moiety may comprise a biological or a chemical group capable of binding another biological or chemical molecule in a medium (e.g., aqueous phase). For example, the binding moiety may include a functional group, such as a thiol, aldehyde, ester, carboxylic acid, hydroxyl, and the like, wherein the functional group forms a bond with the analyte. In some cases, the binding moiety may be an electron-rich or electron-poor moiety wherein interaction between the analyte and the binding moiety comprises an electrostatic interaction. In some cases, the interaction between the analyte and the binding moiety includes binding to a metal or metal-containing moiety.

In some embodiment, the binding moiety and analyte interact via a binding event between pairs of biological molecules including proteins, nucleic acids, glycoproteins, carbohydrates, hormones, drugs, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of binding moieties include peptides, proteins, DNA, RNA, PNA. Other binding moieties and binding pairs are also possible. Binding moieties can also be attached to polymers, organic nanoparticles, inorganic nanoparticles, or metal nanoparticles.

In some embodiments, the binding moiety and the tether interact via a binding event between pairs of biological molecules including proteins, nucleic acids, glycoproteins, carbohydrates, hormones, and the like. In other embodiments the binding moieties can be also bound to a nanoparticle.

In an exemplary embodiment, the binding moiety comprises a protein. In some embodiments, the protein is a hyperthermophilic protein.

The analyte may comprise any suitable material (e.g., a vapor analyte, a liquid analyte, a solid analyte) such that the incorporation of the analyte into the system causes at least a portion of the plurality of Janus droplets to change orientation (e.g., via breaking of a tether and/or agglutination of the Janus droplets). Those skilled in the art would be capable of selecting analytes and components suitable for Janus droplets based upon the teaching of the specification and the examples below. Non-limiting examples of analytes include a biological compound, a drug, a macromolecule, a salt, an electrolyte, an enzyme, a nucleic acid, a carbohydrate, a peptide, a protein, a lipid, a phosphate, a sulfonate, a virus, a pathogen (e.g., bacteria, virus), an oxidant, a reductant, a toxin, a chemical warfare agent, an explosive, carbon dioxide, a surfactant, or combinations thereof. In some embodiments, the tether is a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. In an exemplary embodiment, the analyte is a bacterium.

In another exemplary embodiments, the analyte is a virus. In some embodiments, the virus is a zika virus.

In an exemplary embodiment, an enzyme may be added to the system comprising a plurality of Janus droplets such that the enzyme interacts with one or more of the components, binding moieties, tethers, and/or amphiphilic compounds present in the plurality of Janus droplets. In some such embodiments, the enzyme may interact with the component, binding moiety, tether, and/or amphiphilic compound (e.g., such as a surfactant which is cleaved in the presence of the enzyme) such that at least a portion of the plurality of Janus droplets change orientation as described herein. In certain embodiments, the Janus droplets change orientation at a particular critical concentration of the analyte.

In another exemplary embodiment, one or more Janus droplets may comprise an amphiphilic compound such as a surfactant that is capable of interacting with a biological analyte. In some such embodiments, the Janus droplet may change orientation in the presence of a biological analyte such that the change in orientation can be detected (e.g., by optical transmission).

In some embodiments, the interaction between a binding moiety and the analyte includes a chemical transformation between the binding moiety and the analyte and/or the binding moiety and a tether. Non-limiting examples of chemical transformations include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible.

As described herein, in some embodiments, the methods and systems comprise an outer phase and a plurality of Janus droplets dispersed within the outer phase. In certain embodiments, the plurality of Janus droplets comprises two or more phases. The two or more phases (e.g., a first phase and a second phase) may be substantially miscible over a range of temperatures (e.g., below a critical temperature, above a critical temperature). The two or more phases may also be substantially immiscible over a different range of temperatures (e.g., above the critical temperature, below the critical temperature) than the range of temperatures over which they are miscible. The use of two or more phases with differing miscibility at different temperatures may allow for the one-step formation (e.g., bulk) of such Janus droplets, unconstrained by the limits of previous methods (e.g., low yield of microfluidic devices, multi-step processes, the need for solvent addition and/or extraction, etc.).

Janus droplets described herein may be formed using any suitable method. For example, in some embodiments, an outer phase material, a first phase, and a second phase are mixed and emulsified, forming an outer phase and a plurality of Janus droplets dispersed within the outer phase. Suitable methods for emulsifying the fluid are known in the art and may comprise sonication, high shear mixing, shaking, passing the fluid through a membrane, or injecting the two or more components into the outer phase through a small diameter channel.

Non-limiting examples of methods for forming Janus droplets are described in more detail in commonly-owned U.S. Patent Publication Number 2016/0151753, entitled "Compositions and Methods for Forming Emulsions", filed Oct. 30, 2015 and in U.S. Patent Publication Number 2016/0151756, entitled "Compositions and Methods for Arranging Colloid Phases", filed Oct. 30, 2016, each of which is incorporated herein by reference in its entirety.

Immiscible, as used herein, refers to two phases having an interfacial tension of greater than or equal to 0.01 mN/m as determined by an inverted pendant drop goniometer. Conversely, miscible, as used herein, refers to two phases having an interfacial tension of less than 0.01 mN/m as determined by an inverted pendant drop goniometer.

The term phase, as used herein, generally refers to a portion of a droplet or fluid comprising a group of substantially similar molecules, and/or a group of substantially similar compounds. Those skilled in the art would understand that is not intended to refer to single molecules or atoms. In some embodiments, the phase is a liquid phase (e.g., an aqueous phase, a non-aqueous phase) comprising a group of substantially similar compounds and/or molecules and/or polymers. For example, in some cases, each phase may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more phases.

In some embodiments, at least one of the two or more phases (e.g., the first phase) comprises a hydrocarbon. Non-limiting examples of suitable hydrocarbons include alkanes (e.g., hexane, heptane, decane, dodecane, hexadecane), alkenes, alkynes, aromatics (e.g., benzene, toluene, xylene, benzyl benzoate, diethyl phalate), oils (e.g., natural oils and oil mixtures including vegetable oil, mineral oil, and olive oil), liquid monomers and/or polymers (e.g., hexanediol diacrylate, butanediol diacrylate, polyethylene glycols, trimethylolpropane ethoxylate triacrylate), alcohols (e.g., butanol, octanol, pentanol), ethers (e.g., diethyl ether, diethylene glycol, dimethyl ether), nitromethane, halogenated liquids (e.g., chloroform, dichlorobenzene, methylene chloride, carbon tetrachloride), brominated liquids, iodinated liquids, lactates (e.g., ethyl lactate), acids (e.g., citric acid, acetic acid), liquid crystals (4-cyano-4'-pentylbiphenyl), trimethylamine, liquid crystal hydrocarbons (e.g., 5-cyanobiphenyl), combinations thereof, and derivatives thereof, optionally substituted. In some embodiments, the hydrocarbon comprises a halogen group, sulfur, nitrogen, phosphorous, oxygen, or the like. Other hydrocarbons and solutes are also possible.

In some embodiments, at least one of the two or more phases (e.g., the second phase) comprises a fluorocarbon. Non-limiting examples of suitable fluorocarbons include fluorinated compounds such as perfluoroalkanes (e.g., perfluorohexanes, perfluorooctane, perfluorodecalin, perfluoromethylcyclohexane), perfluoroalkenes (e.g., perfluorobenzene), perfluoroalkynes, and branched fluorocarbons (e.g., perfluorotributylamine). Additional non-limiting examples of suitable fluorocarbons include partially fluorinated compounds such as methoxyperfluorobutane, ethyl nonafluorobutyl ether, 2H,3H-perfluoropentane, trifluorotoluene, perfluoroidodide, fluorinated or partially fluorinated oligomers, 2,2,3,3,4,4,5,5,6,6,7,7,8,8,9,9-hexadecafluorodecane-1,10-diyl bis(2-methylacrylate), perfluoroiodide, and 2-(trifluoromethyl)-3-ethoxydodecafluorohexane. Other fluorocarbons are also possible.

In some embodiments, at least one of the two or more components phases a silicone such as silicone oil. Non-limiting examples of suitable silicone oils include polydimethylsiloxane and cyclosiloxane fluids.

In some embodiments, at least one of the two or more phases comprises water.

In some embodiments, at least one of the two or more phases comprises an ionic liquid (e.g., an electrolyte, a liquid salt). In some embodiments, at least one of the two or more inner phases comprises an ionic liquid (e.g., an electrolyte, a liquid salt, 1-allyl-3-methylimidazolium bromide, 1-allyl-3-methylimidazolium chloride, 1-benzyl-3-methylimidazolium hexafluorophosphate, 1-butyl-1-methylpyrrolidinium hexafluorophosphate). In some embodiments, the outer phase comprises water. In certain embodiments, at least one of the two or more phases comprises a deuterated compound (e.g., a deuterated hydrocarbon).

In some embodiments, at least one of the two or more phases comprises a chlorinated solvent (e.g. chloroform, carbon tetrachloride).

In some embodiments, at least one of the two or more phases comprises a combination of the materials described above (e.g., comprising a hydrocarbon, a fluorocarbon, a silicone, or combinations thereof). Non-limiting examples of combinations of phases present in the Janus droplets described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

Those skilled in the art would be capable of selecting suitable phases based upon the teachings of the specification and the examples below such that the two or more phases are immiscible under a particular range of temperatures and/or conditions, as described above.

The outer phase may comprise any suitable material. Generally, the two or more phases comprising the plurality of Janus droplets may be substantially immiscible with the outer phase. In some embodiments, the outer phase is an aqueous phase (e.g., comprising water). The aqueous phase may, in some cases, have ions and/or be mixed with a biological fluid (e.g., sputum, blood, plasma, urine). In certain embodiments, the outer phase is a non-aqueous phase. In some embodiments, the non-aqueous phase comprises a hydrocarbon, a fluorocarbon, a silicone, or the like, as described above in the context of the two or more phases, substantially immiscible with the two or more phases. Those skilled in the art would be capable, based upon the teachings of the specification and the examples below, of selecting suitable materials for use as an outer phase based upon the miscibility of those materials (e.g., such that the two or more phases are substantially immiscible with the outer phase). The use of a non-aqueous outer phase may be advantageous in certain applications where the emulsion is used in low humidity environments. For example, a plurality of Janus droplets comprising fluorocarbon/hydrocarbon phases can be created in a liquid silicone matrix.

In some embodiments, the Janus droplet comprises an amphiphilic compound. In certain embodiments, the binding moiety is associated with the amphiphilic compound. For example, the binding moiety may be bound to at least a portion of the amphiphilic compound.

In certain embodiments, the amphiphilic compound is miscible in the outer phase. In some embodiments, the amphiphilic compound is miscible in at least one of the two or more phases (e.g., the first phase, the second phase). In certain embodiments, the amphiphilic compound has a greater miscibility in at least one of the two or more phases than a miscibility in the outer phase. In other embodiments the amphiphilic compound is added to the Janus droplet though a dispersion, such as an aqueous micelle structure or dissolution method (e.g., comprising injecting a dispersion of the amphiphilic compound into the solution containing the Janus droplets). In some embodiments, the amphiphilic compound is disposed at the interface between the outer phase and the plurality of Janus droplets. Amphiphilic compounds may also be generated, in some embodiments, by reaction of a solute in one phase with solute in another phase. For example, without wishing to be bound by theory, a reactive group in an organic phase may, in some cases, react with a solute from an aqueous phase to create a amphiphilic molecule at the surface of a droplet. In certain embodiments, the amphiphilic compound is disposed at the interface between at least two of the two or more phases (e.g., the interface between the first phase and the second phase). The amphiphilic compound may preferentially interact with one or more phases or the outer phase. Those skilled in the art would be capable of selecting a suitable amphiphilic compound based upon the teachings of the specification and examples below.

In some embodiments, the amphiphilic compound is a surfactant. Non-limiting examples of suitable surfactants include ionic surfactants, non-ionic surfactants, and zwitterionic surfactants. In some embodiments, the surfactant is a fluorosurfactants (e.g., commercially available fluorosurfactants such as Zonyl® or Capstone®). In certain embodiments, the surfactant is anionic surfactants (e.g., sodium dodecyl sulfate (SDS)), cationic surfactants (e.g., alkyltrimethyl ammonium chloride, alkylmethyl ammonium bromide), non-ionic surfactants (e.g., alkyl poly(ethylene oxide)), zwitterionic surfactants (e.g., alkyl betain, C8-lecitin), polymeric surfactants, gemini surfactants, particulate surfactants (e.g., graphene oxide, silica particles, gold nanoparticles, polymer nanoparticles), and combinations thereof. Other surfactants are also possible. In some embodiments, the amphiphilic compound is a nucleic acid (e.g., DNA, RNA). In certain embodiments the amphiphilic compound comprises an amino acid (e.g., a peptide, a protein). In some embodiments, the amphiphilic compound comprises a biomaterial.

Non-limiting examples of suitable biomaterials include carbohydrates or derivatives thereof, saccharides or derivatives thereof (e.g., sialic acid), lipids or derivatives thereof, enzymes, chromophores or the like. Those skilled in the art would be capable of selecting suitable biomaterials based upon the teachings of the specification and the examples below.

In some embodiments, the amphiphilic compound comprises a perfluorinated segment. In some embodiments, the amphiphilic compound comprises ethylene glycol.

In some embodiments, the amphiphilic compound is capable of forming metal complexes.

In some embodiments, the amphiphilic compound is gallic acid. In some embodiments, the amphiphilic compound comprises polystyrene-b-polyacrylic acid or a derivative thereof.

In some embodiments, the one or more phases (e.g., the first phase, the second phase) and/or the outer phase comprises an additional compound dispersed in the one or more phases and/or the outer phase. In certain embodiments, the additional compound is miscible/dispersible in the first phase and immiscible/not dispersible in the second phases. In some cases, at least a portion of the additional compound is dispersible in the first phases and not dispersible in the second phases (e.g., a surfactant). In some embodiments, the additional compound may be dispersible or not dispersible in the outer phase. Non-limiting examples of suitable additional compounds include particles (e.g., magnetic particles/nanoparticles, silica particles), biological molecules (e.g., insulin), pharmaceutical compounds, polymers, surfactants, cells, bacteria, viruses, active pharmaceutical ingredients, and metals or metal particles. Other additional compounds are also possible and those skilled in the art would be capable of selecting such compounds based upon the teachings of this specification.

In some embodiments, the plurality of Janus droplets can be formed by adjusting the temperature of a fluid comprising the outer phase and the two or more immiscible phases such that the two or more phases become substantially miscible with each other, and emulsifying the fluid (e.g., thus forming the plurality of Janus droplets). In certain embodiments, the method comprises adjusting the temperature of the fluid comprising the two phases such that the two or more phases become substantially immiscible. In other embodiments, the method comprises the addition of a solvent that creates a stable uniform composition prior to emulsification, and the solvent is removed by evaporation or extraction to give phase separation and produce a Janus droplet.

Figure 3:
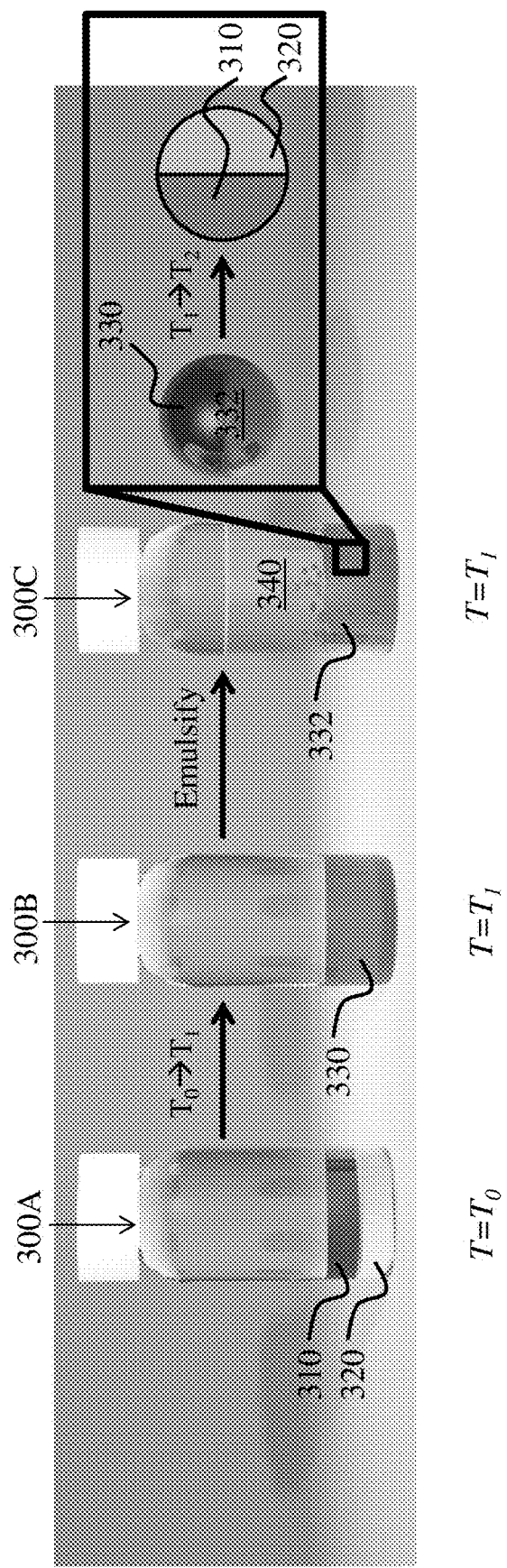
FIG. 3 illustrates the formation of Janus droplets, according to one set of embodiments.

For example, as illustrated in FIG. 3, a fluid 300A comprises first phase 310 (e.g., a hydrocarbon) and second phase 320 (e.g., a fluorocarbon) which are immiscible at a first temperature $T_0$. In some embodiments, To is adjusted to a second temperature $T_1$ (e.g., where $T_1$ is greater than $T_0$, or where $T_1$ is less than $T_0$) such that the first component and second component form a miscible mixture 330 in fluid 300B. For example, in some embodiments, the first phase and the second phase, which are initially substantially immiscible, may be heated such that they are miscible. In certain embodiments, the first phase and the second phase, which are initially substantially immiscible, may be cooled such that they are miscible. Miscible mixture 330 can, in certain embodiments, be emulsified to form emulsion 300C comprising plurality of droplets 332. Plurality of droplets 332 may comprise miscible mixture 330 and be present in an outer phase 340. In some cases, outer phase 340 may be added prior to changing the temperature from $T_0$ to $T_1$. In certain embodiments, outer phase 340 may be added after changing the temperature but prior to emulsification.

In some embodiments, $T_1$ is adjusted to a temperature $T_2$ (e.g., where $T_2$ is greater than $T_1$ or where $T_2$ is less than $T_1$) such that droplet 332 comprises first phase 310, and second phase 320 substantially immiscible with first component 310, forming a Janus droplet.

In some embodiments, $T_1$ is greater than a critical temperature of the two or more phases (e.g., an upper consolute temperature of the two or more phases). In certain embodiments, $T_1$ is less than a critical temperature of the two or more phases (e.g., a lower consolute temperature). Those skilled in the art will be capable of selecting suitable methods for determining the critical temperature (e.g., the upper consolute temperature, the lower consolute temperature) of two or more phases.

Suitable methods for emulsifying the fluid are known in the art and may comprise sonication, high shear mixing, shaking, passing the fluid through a membrane, or injecting the two or more components into the outer phase through a small diameter channel.

The plurality of Janus particles may have any suitable average cross-sectional dimension. In some embodiments, the average cross-sectional dimension of the plurality of Janus particles is greater than or equal to 400 nanometers, greater than or equal to 500 nanometers, greater than or equal to 600 nanometers, greater than or equal to 800 nanometers, greater than or equal to 1 micron, greater than or equal to 2 microns, greater than or equal to 5 microns, greater than or equal to 10 microns, greater than or equal to 20 microns, greater than or equal to 30 microns, greater than or equal to 50 microns, greater than or equal to 60 microns, greater than or equal to 75 microns, greater than or equal to 100 microns, greater than or equal to 150 microns, greater than or equal to 200 microns, greater than or equal to 300 microns, or greater than or equal to 400 microns. In certain embodiments, the average cross-sectional dimension of the plurality of Janus particles may be less than or equal to 500 microns, less than or equal to 400 microns, less than or equal to 300 microns, less than or equal to 200 microns, less than or equal to 150 microns, less than or equal to 100 microns, less than or equal to 75 microns, less than or equal to 60 microns, less than or equal to 50 microns, less than or equal to 20 microns, less than or equal to 10 microns, less than or equal to 5 microns, less than or equal to 2 microns, less than or equal to 1 micron, less than or equal to 800 nanometers, less than or equal to 600 nanometers, or less than or equal to 500 nanometers. Combinations of the above-referenced ranges are possible (e.g., greater than or equal to 400 nanometers and less than or equal to 500 microns, greater than or equal to 400 nanometers and less than or equal to 100 microns, greater than or equal to 30 microns and less than or equal to 200 microns). Other ranges are also possible.

EXAMPLES

The following examples illustrate embodiments of certain aspects of the invention. It should be understood that the methods and/or materials described herein may be modified and/or scaled, as known to those of ordinary skill in the art.

The following examples demonstrate the use of systems for the detection of analytes.

Surfactants specially designed with recognition elements to bind targeting analytes (species/molecules of interest) multivalently were synthesized. The binding interaction was able to transform a plurality of Janus droplets from an upright position to a horizontally tilted position against gravity. This transformation generated a distinct optical signal (scattering of a light beam) in the presence of analytes. The opposite response was also possible wherein a plurality of Janus droplets were pre-titled by binding to a surface or particle and is initially in a scattering position. In this case, the action of an analyte was to disrupt the linkage between the surface or particle and allow a relaxation to an upright position that allowed for reduced scattering. The optical signal could be recorded via a smartphone by for example using a QR code for binary on/off detection, using low magnification images that are processed computationally to quantify the amount of analytes in the emulsion mixture, and/or the monitoring the transmission of focused light beams through the samples. Such systems could be used in biosensor applications including aqueous liquid phase detection. The emulsions (comprising Janus droplets) with only low molecular weight surfactant molecules were relatively inexpensive to fabricate and stable over multiple weeks with no further precautions. In cases where greater emulsion stability may be required, polymeric surfactant molecules and structures could be employed. Additionally, the Janus droplets were highly selective and sensitive for detection of pathogens as, in some cases, small changes in the concentration and/or the identity of the surfactants lead to significant changes in the orientation of the Janus droplets. Janus droplets were fabricated using either bulk emulsification, which generated polydisperse droplets, or in a microfluidic device, which generated monodisperse droplets. For surfactants soluble in water, a solution containing the functionalized surfactants was used as the continuous phase. Hydrocarbon phase (such as hexane, ortho-dichlorobenzene, phthalate, etc.) and fluorocarbon phase (such as perfluorohexane, ethyl nonafluorobutyl ether, methoxy perfluorobutane) were mixed and heated over the upper critical temperature to generate the single droplet phase. When the droplet phase was dispersed into the continuous (outer) phase containing surfactants, single emulsions were generated; and upon cooling, the hydrocarbon and fluorocarbon phases separated to generate Janus droplets. The composition of each droplet was substantially similar because they were generated from the same single droplet phase. In addition, surfactants were able to be incorporated into the droplet phase. Surfactants that were not soluble in water were dissolved in the hydrocarbon phase or the fluorocarbon phase before mixing. The droplet phase containing surfactants could then be dispersed into the continuous water phase, which may contain additional surfactants and surfactant assemblies to generate the droplets. In both cases, Janus droplets were used as sensing particles with surfaces covered by with functionalized surfactants. The surfactants or surfactant assemblies could contain polymer surfactant/stabilizers or macromolecules of biological significance, including proteins, enzymes, nucleic acids, DNA, RNA.

Sensing of Pathogenic Bacteria

Figure 4A:
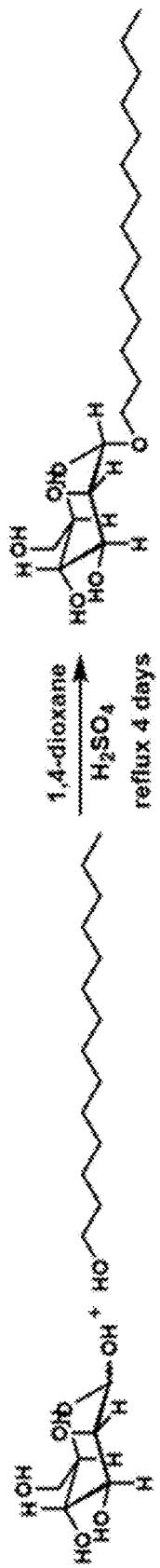
FIG. 4A shows an exemplary surfactant for use in a system including Janus droplets, according to one set of embodiments.
Figure 4B:
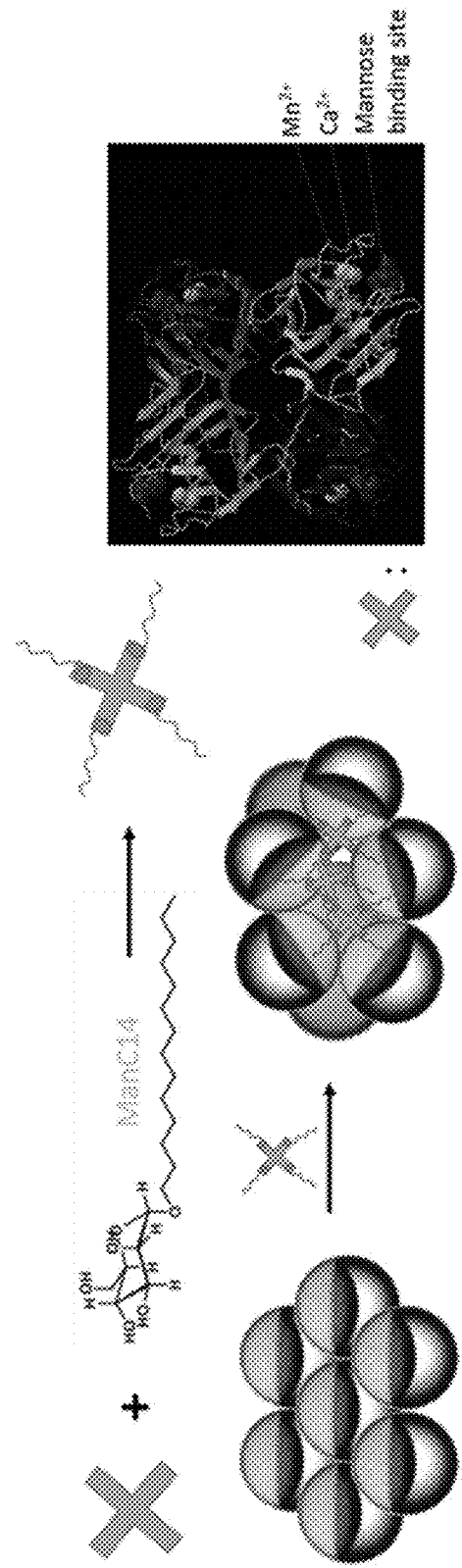
FIG. 4B shows the agglutination of a plurality of Janus droplets in the presence of analyte, according to one set of embodiments.

Our approach to detect pathogenic bacteria took advantage of the general affinity that different bacteria exhibit for specific patterns of carbohydrate. One of the targeting analytes, *Escherichia coli* (*E. coli*), is a bacterium that can be easily spread in contaminated food and water. While most strains of *E. coli* are harmless, certain strains that produce toxins could cause serious and fetal illness. To detect the *E. Coli* bacteria, surfactants were carefully designed that interact with the surfaces of the cell via the carbohydrate-lectin interaction. This weak interaction between lectin on the surfaces of *E. coli* and D-mannose typically creates a challenge to detect bacteria with high sensitivity when relying on a single interaction. Thus, a surfactant that functionalizes one phase of the Janus droplets to increase the concentration of the mannose moiety on the surface was designed. The increase in the concentration of the mannose moiety significantly enhanced binding affinity between the bacteria and the droplets, transforming a droplet into a selective sensing particle. The binding between Concanavalin A (ConA), a lectin known to bind D-mannose, was initially investigated using the Janus droplets as a model system. This technology could be relatively easily adapted for other analytes by, for example, changing the active surfactants. A novel surfactant bearing a D-mannose head group (ManC14) was synthesized (FIG. 4A). FIG. 4A shows the scheme for Mannose surfactant (ManC14) synthesis. FIG. 4B shows a schematic illustration of Janus droplets aligning with Concanavalin A (ConA). The denser perfluorohexane phase aligned at the bottom and the hexane on the top of the Janus droplets.

For this particular sensing platform, the Janus droplets were fabricated using the following method. The surfactants ManC14 and Zonyl® FS 300 (a commercially available fluorocarbon surfactant) were dissolved in a HEPES buffer solution (pH=7.5) as the continuous phase. A mixture of hexane and perfluorohexane (single droplet phase) was dispersed into the surfactant solution and cooled down to generate Janus droplets. The hexane phase on the Janus droplets was functionalized with mannose groups where the surfactant ManC14 aligned preferentially at the hexane/water interface. Without wishing to be bound by theory, due to gravity and the higher density of perfluorohexane in relative to that of hexane, Janus droplets aligned with perfluorohexane phase in the bottom (FIG. 4B). ConA was dissolved in HEPES buffer solution with final concentration of 0.5 mg mL$^{-1}$. An increasing amount of this solution (10 μL to 40 μL) was added to the Janus droplets; and after swirling the solution, the two-faced Janus droplets started aligning in a unique tilted configuration. The surfaces that were stabilized by ManC14 surfactant agglutinated together to form droplet complexes (FIG. 4B).

Without wishing to be bound by theory, the agglutination phenomenon occurred because ConA has four subunits, each with a binding site for mannose. This four-site binder acted similarly to an antibody that binds multiple particles and joins them together to make agglutinated droplet complexes. When Janus droplets agglutinate, the solution changes from transparent to opaque. This large and easily observable change is particularly powerful because detection events will not generally require, for example, any external power input. The Janus droplet agglutination level could be characterized both qualitatively and quantitatively as described herein.

Tuning the Surface Chemistry

Surface recognition is a general phenomenon that can be applied to many different types of methods. The use of a ligand surfactant binding with a multivalent receptor, which can be a protein, cell, or pathogen, nanoparticle was described above. This scheme can be reversed where a receptor is immobilized at the surface of a droplet and then use a multivalent ligand scaffold (natural or synthetic) to bind the Janus droplets and hold them in a tilted (scattering) state relative to the aligned non-scattering state favored by gravity. The ligands can be designed to have a lower affinity than a target analyte and hence exposure to the analyte can result in a displacement that breaks the linkage (e.g., tether) between the polyvalent ligand and the droplet. Similarly, the tether between the droplet and the ligand can be cleaved. This could be affected by an enzyme that cleaves a peptide, such as an ester or a degraded RNA. It could also be affected by catalytic or heavy metal ions or select nucleophiles (sulfides). In some cases, the ligands could be bound to a surface. It is also possible that the ligands reside on another droplet.

Individual droplets that are tilted or alternatively not tilted (aligned by gravity) can be relatively easily quantified. This gives rise to the ability to, in some cases, detect single analytes. For example, it is possible that a single molecule of DNA can be detected if the droplet is anchored to a surface by a DNA duplex. Disruption of this duplex by a complementary target DNA analyte can be observed. One aligned droplet in a sea of other tilted droplets would be readily detected. This scheme has an advantage that, for example, there would be many potential binding sites for the DNA molecule and hence thus the target DNA would not be required to find a rare binding site. Similarly, a cluster of tilted droplets in a sea of aligned droplets can be detected and, in doing so, would be able to detect a single analyte.

Detection of Agglutinated Janus Droplets

Figure 5B:
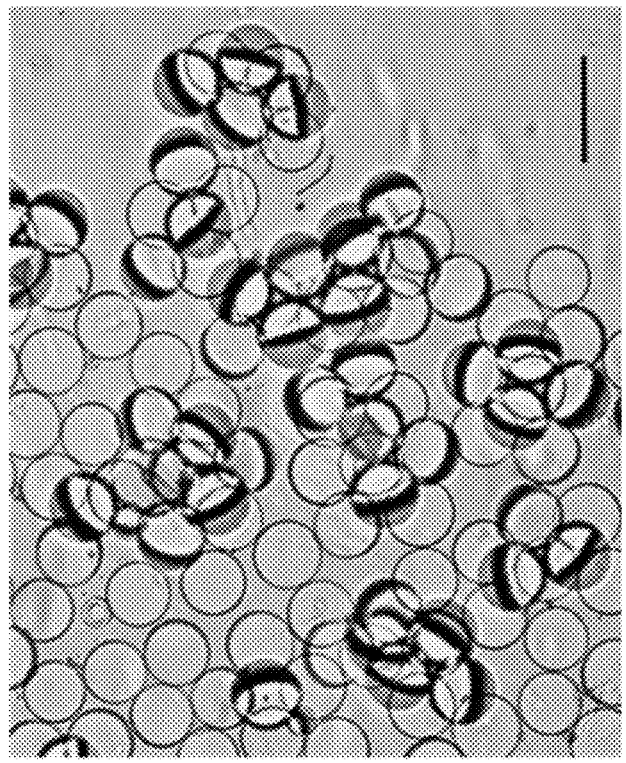
FIG. 5B shows a plurality of Janus droplets with altered orientation, according to one set of embodiments.
Figure 5A:
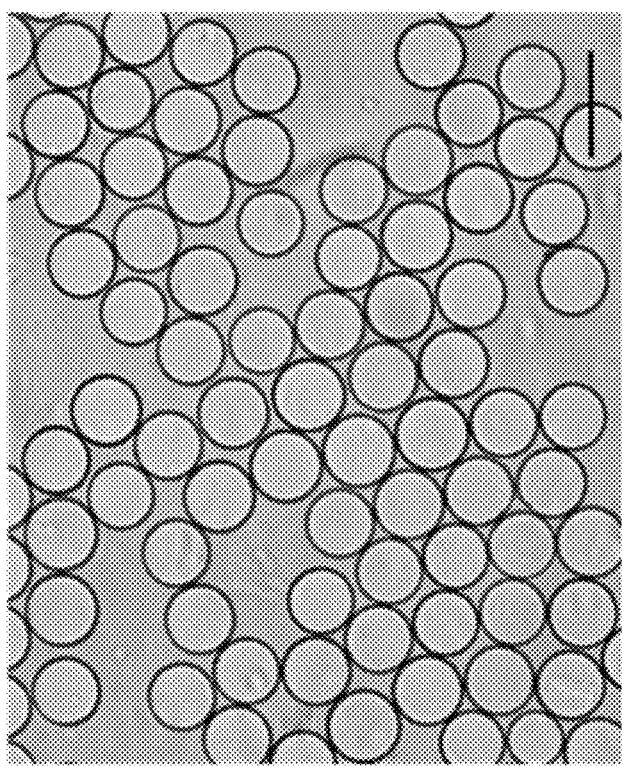
FIG. 5A shows a monodispersed plurality of Janus droplets, according to one set of embodiments.
Figure 6A:
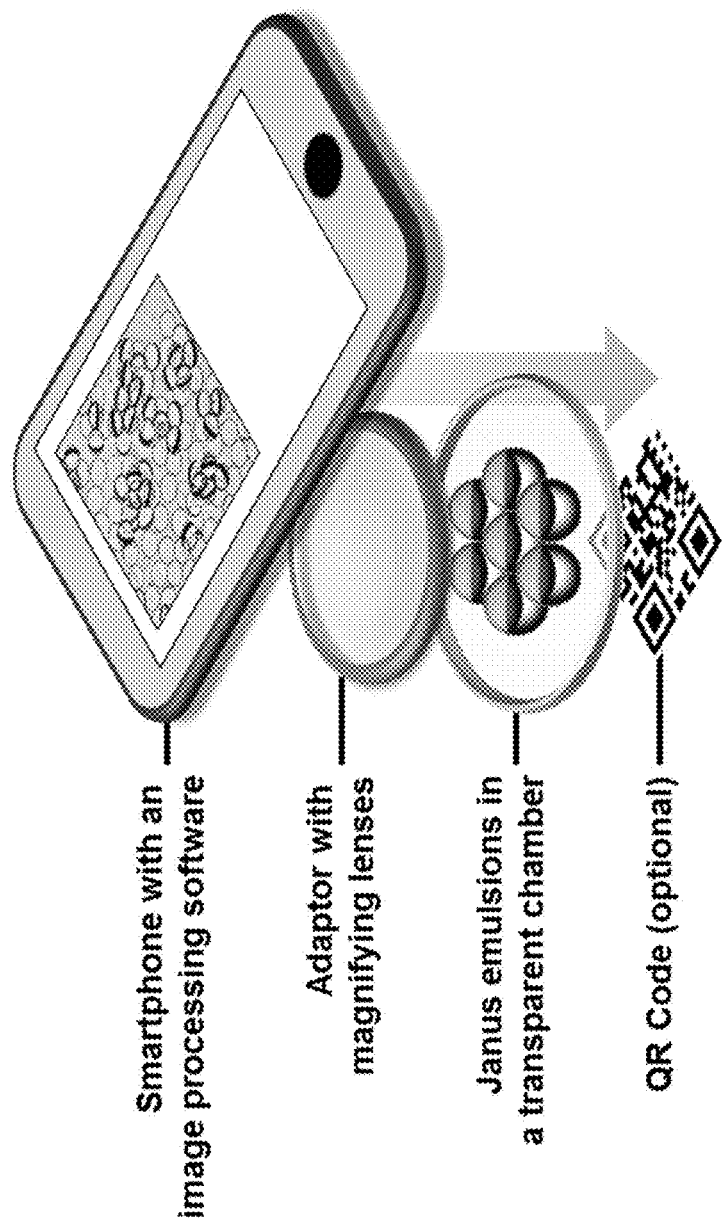
FIGS. 6A-6B show an exemplary system comprising a plurality of Janus droplets which, upon exposure to an analyte, changes an optical property of the system, according to one set of embodiments.

The solution of Janus droplets generally turns from transparent to opaque when the emulsions are agglutinated. FIG. 5A shows a solution of Janus droplets before exposure to an analyte. FIG. 5B shows a solution of Janus droplets after exposure to the analyte. Such large and easily observable differences may be incorporated into the use of image processing algorithms to analyze the optical micrographs. These optical micrographs are readily taken from, for example, any common smartphone equipped with magnifying lenses to enable low-magnification of 4× and 10× (FIG. 6A).

Figure 6B:
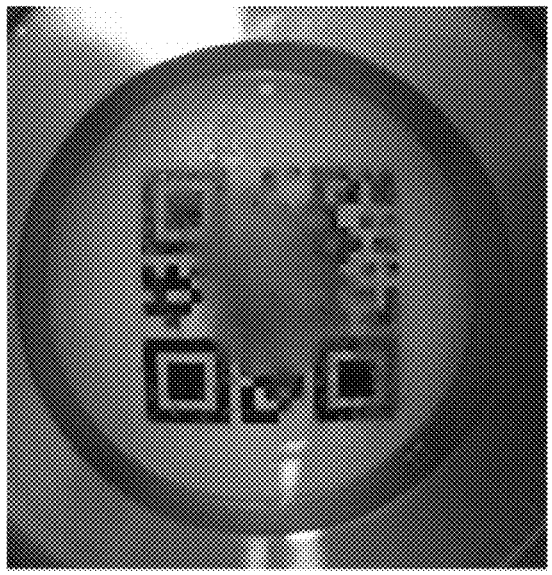
Figure 6B:

For qualitative purposes, the detection may use the significant changes in the optical transparency between pristine and agglutinated Janus droplets to generate a binary response. For example a transparent analysis chamber containing the Janus droplets was placed on top of a two-dimensional QR code, as shown in FIG. 6B. In the presence of ConA, the chamber became opaque and covered a portion of the QR code. This transformation inhibited a smartphone from reading the QR code.

Figure 7A:
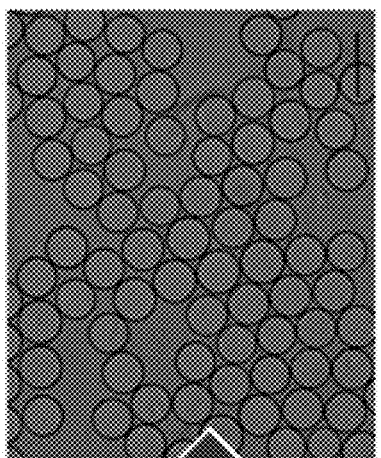
FIGS. 7A-7F show image processing based of Janus droplets upon exposure to an analyte, according to one set of embodiments.
Figure 7B:
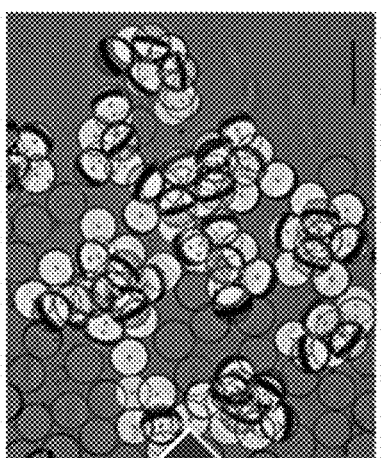
Figure 7C:
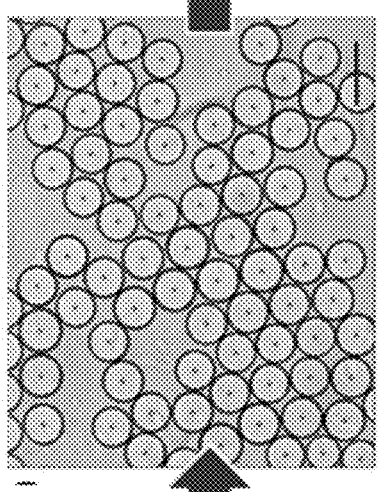
Figure 7D:
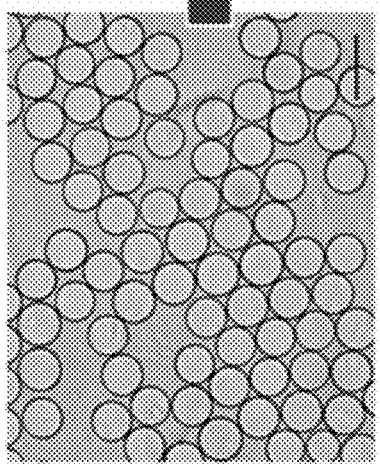
Figure 7E:
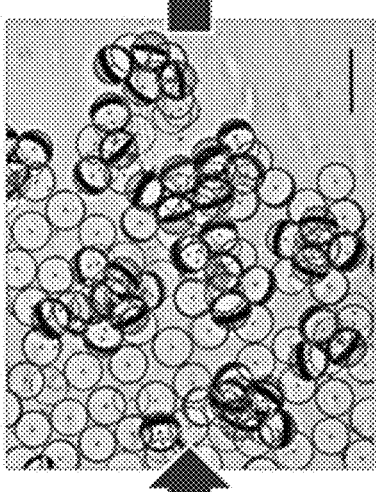
Figure 7F:
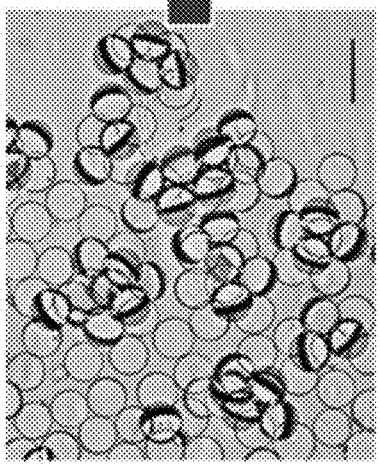
Figure 8A:
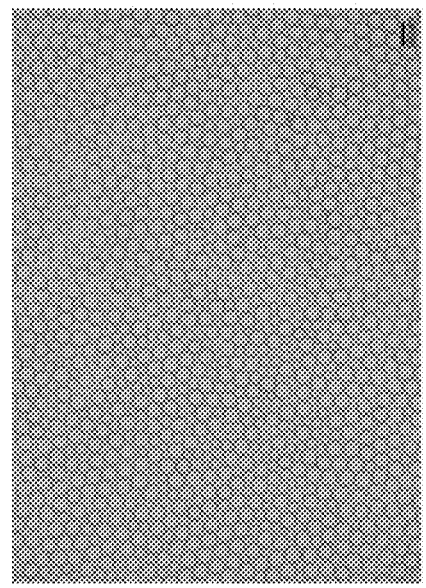
FIGS. 8A-8F show image processing based of Janus droplets upon exposure to an analyte, according to one set of embodiments.
Figure 8B:
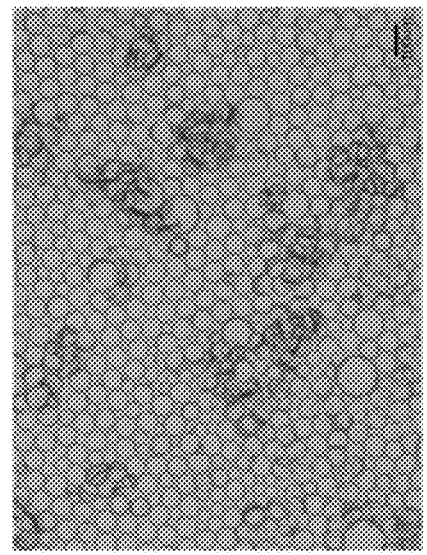
Figure 8C:
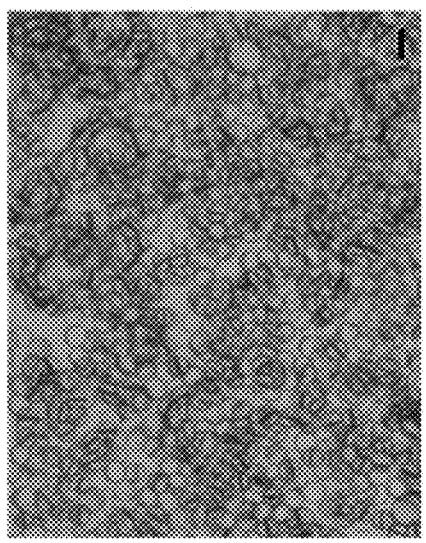
Figure 8D:
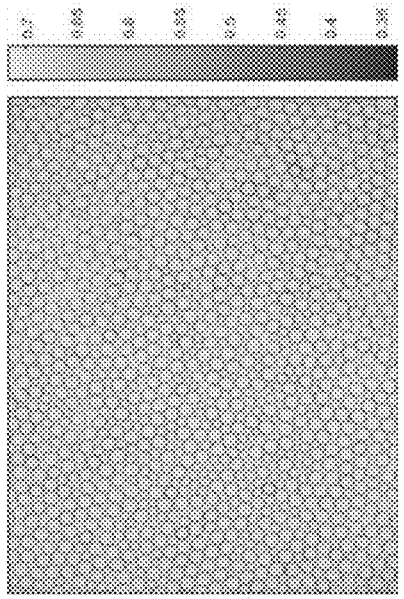
Figure 8E:
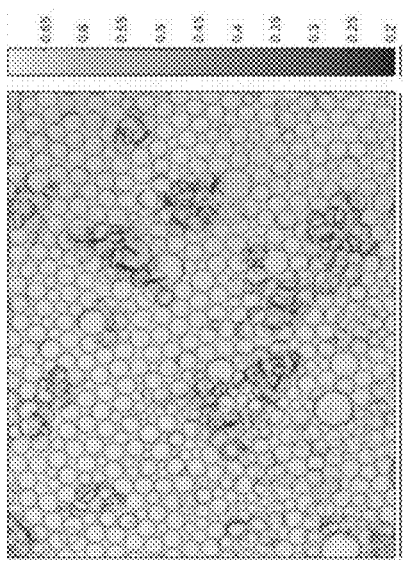
Figure 8F:
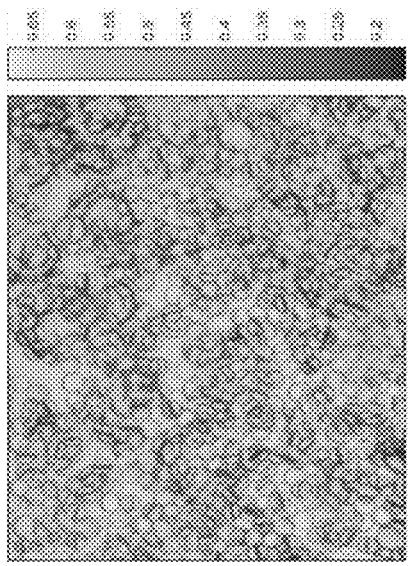

To quantify the degree of agglutination, an image processing program that calculates the percentage of area covered by agglutinated Janus droplets by two distinct logics was implemented: 1) the amount of overlapping droplets and 2) the difference in optical intensity of the images. FIGS. 7A-7C show the quantification of a plurality of Janus droplets in the absence of a targeted analyte. FIGS. 7D-7F show the quantification of a plurality of Janus droplets exposed to a targeted analyte.

Specifically, the image processing program analyzed the raw optical micrographs (FIG. 7A and FIG. 7D) by mapping out the locations of each Janus droplet and measuring their radii (FIG. 7B and FIG. 7E). Using this information, the program then sought overlapping emulsions. As described above, during agglutination the Janus droplets joined together to form droplet complexes of agglutinated Janus droplets. The program distinguished each droplet with more than two overlapping neighbors as a part of a droplet complex and rejected any droplet with zero, one, or two overlapping neighbors (FIG. 7C and FIG. 7F). The percentage of area covered by agglutinated Janus droplets were then calculated for both pristine sample (FIG. 7C) and agglutinated sample (FIG. 7F).

The area covered by these Janus droplet agglutinations were then further correlated with the analysis of optical intensity within the images. Similar to the qualitative detection, the image analysis can distinguish regions of agglutinated Janus droplets due to the lower optical transparency. The program used an adaptive thresholding algorithm to distinguish areas with higher transparency (pristine Janus droplets) from the opaque regions (agglutinated Janus droplets), FIGS. 8A-8F. The combination of the two distinct logics—identifying the overlapping Janus droplets and analyzing changes in optical intensity—can accurately detect the regions of agglutinated Janus droplets. Furthermore, the whole process can be completed within seconds from capturing the image to final calculation.

In some cases, the Janus droplets behave as individual lenses. Such droplets can be interrogated with a scanning light beam or a number of beams simultaneously. In this case (e.g., FIGS. 8A-8F), the light beams transmit through the sample and impinge on an array of light detectors. Signals can be deduced by changes in the intensity that represents the straight path of the light beam and the light that is refracted (e.g., deviating from a straight path). Without wishing to be bound my theory, lower intensity at the point of the straight path and higher intensity of light that is refracted from that path, indicate an increase in the tilt of one or more droplets. Similarly, higher intensity of light in the straight path and lower intensity that has been refracted may indicate a decrease in the tilt of the droplet. Such lensing permits detection of changes in a single droplet. For example, the ability to detect single events that can lead to the detection of single pathogens, cells, catalysts, or molecules.

Figure 9:
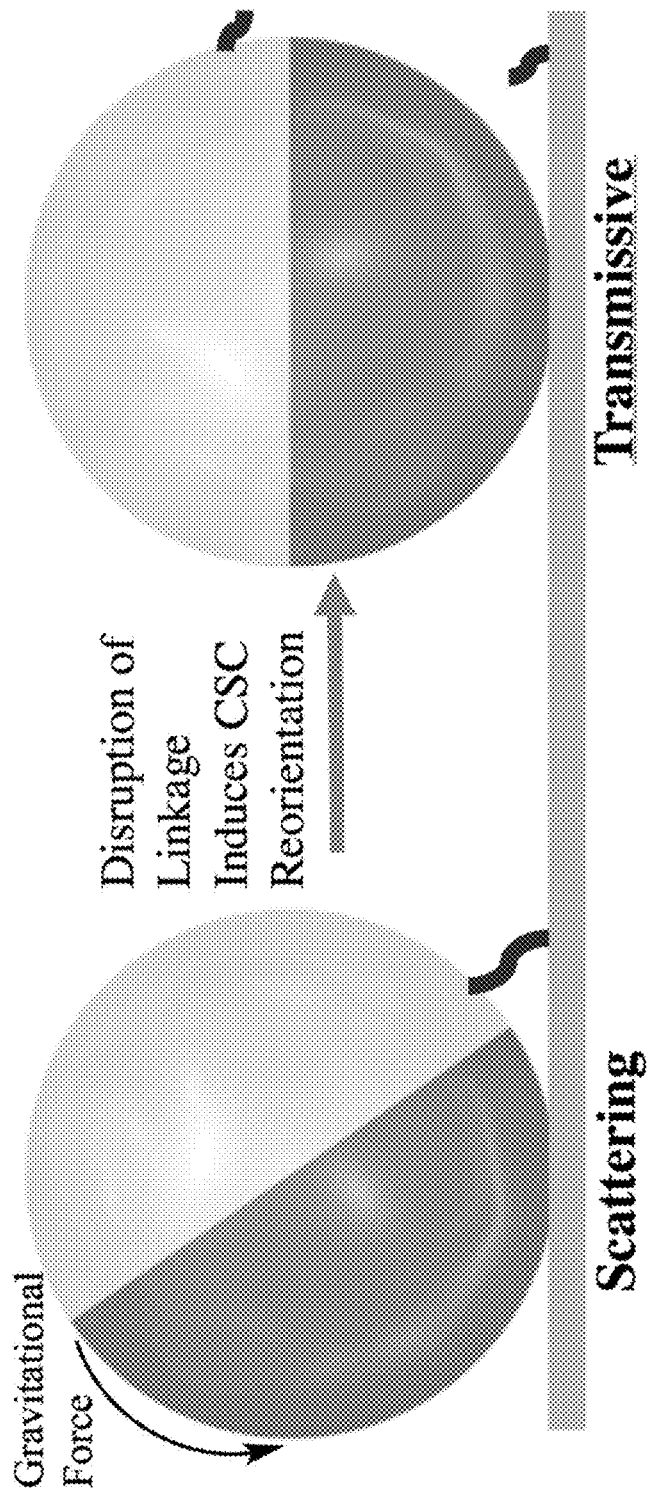
FIG. 9 shows an illustrative embodiment of interaction with an analyte resulting in the change of orientation of a Janus droplet, according to one set of embodiments.

FIG. 9 details a strategy wherein breaking a single linkage (tether) can potentially generate a sensor response that is visible to the naked eye. In this system, the red phase of the Janus droplet (CSC) had a higher density, and a gravitational force worked to orient the particles. Disrupting a chemical bond or complementary DNA interaction tehter, which has pinned the Janus droplet in a tilted scattering configuration, produced a relaxation to the transmissive equilibrium orientation. An advantage of this method is, for example, that only one droplet in a multitude of droplets need be rotated to be detected. Additionally by tethering to patterned surfaces, arrays of sensors can be produced that can detect multiple types of analytes in a single device.

Formation of Droplets

Materials. For the detection of ConA, hexane and perfluorohexane were chosen as the hydrocarbon and fluorocarbon phases respectively. In other cases, different pairs of hydrocarbon (ortho-dichlorobenzene, phthalate, etc.) and fluorocarbon (ethyl nonafluorobutyl ether, methoxy perfluorobutane, etc.) phases can be substituted to tune the upper critical temperature ($T_c$) of the mixture and the differences in density for suitable applications. For the continuous water phase, surfactants ManC14 and Zonyl® FS 300 were chosen to stabilize and generate the Janus droplets. The two surfactants were dissolved in HEPES buffer solution (pH=7.5) separately with concentration of 0.0005% and 0.01% by weight, respectively. In both bulk emulsification and microfluidics method, the final volume ratio between ManC14 solution and Zonyl FS 300 solution was kept at 1.2:1 to generate two-hemisphere Janus droplets. For surfactants that are soluble in water (such as ManC14 and Zonyl® FS 300), a solution containing the functionalized surfactants was used as the continuous phase.

Bulk emulsification for polydispersed Janus droplets. To generate Janus droplets via bulk emulsions, we began by preparing an equal-mixture of hexane and perfluorohexane with a total volume of 1 mL in a 5 mL glass vial. The mixture initially formed an immiscible solution at room temperature. The vial containing the mixture was then heated to above the $T_c$ using a standard heat gun until the mixture was miscible; for hexane-perfluorohexane mixture, the $T_c$ is 20° C. For other combinations of hydrocarbon and fluorocarbon, the $T_c$ may vary depending on the two liquids. In another 5 mL glass vial, 1 mL of the continuous phase containing ManC14 and Zonyl FS 300 (concentrations of both reported in the previous section) was also heated to the same temperature as the vial containing hexane-perfluorohexane mixture. This precaution may mitigate the phase segregation of hexane and perfluorohexane upon addition before emulsification. 50 uL of heated and miscible hexane-perfluorohexane mixture was then injected into the heated continuous phase via a pipette. The Janus droplets were then generated by shaking the vial using a vortex mixer at 3000 RPM for 5 seconds. The solution of Janus droplets was then cooled down below $T_c$ using an ice bath. This method of bulk emulsification generated polydispersed droplets with diameters ranging from 30 to 200 µm as observed by an optical microscope.

Generation of monodispersed Janus droplets via microfluidics. Both coaxial glass capillary microfluidics and commercial available microfluidic chips were used to generate emulsions. For coaxial glass capillary microfluidics, devices were made from an outer square capillary (OD=1.5 mm, ID=1.05 mm, AIT Glass) and inner cylindrical capillary (OD=1 mm, World Precision Instruments) pulled to a 30 µm tip using a P-1000 Micropipette Puller (Sutter Instrument Company). For commercial microfluidic device, Focused Flow Droplet Generator chip (channel width=100 µm, channel depth=20 µm, tip width=10 µm, glass) from Micronit was used. In both microfluidics system, Harvard Apparatus PHD Ultra syringe pumps were used to inject the outer phase (continuous phase) and inner phase (droplet phase). The flow rates were 50 µL min$^{-1}$ for the continuous phase and 30 µL min$^{-1}$ for the droplet phase. The solution of monodispersed droplets was first collected via 20 mL glass vial and later diluted with both ManC14 solution and Zonyl® solution to achieve a final droplet phase concentration of 6% by volume while maintaining the 1.2:1 volume ratio of the two surfactants. The microfluidic setup was heated above the $T_c$ of the inner phase solution using a heat lamp. Janus droplets were then cooled below $T_c$ to induce phase separation. For hexane-perfluorohexane emulsions, the emulsions were chilled on ice prior to imaging and often imaged while immersed in a cool water bath to maintain a temperature below 20° C. The average diameter of the monodispersed droplets generated from this setup were 60±10 µm. The composition of each droplet was nearly identical because each droplet was generated from the same single droplet phase.

Stability and sample storage. The Janus droplets generated from either method described above were observed to be stable on the order of weeks under room temperature. After emulsification, the Janus droplets were kept within the continuous phase at room temperature in a closed glass vial without mechanical perturbation. The diameter of the Janus droplets was not observed to change significantly after weeks of storage.

Sensing

Sample preparation for sensing of ConA. Monodispersed or polydispersed Janus droplets used for sensing experiments were fabricated using methods described above. Janus droplets were loaded into a stainless steel sample holder with a 1 cm deep well and a 1.5 cm diameter viewing window. 0.5 mL of mixed surfactant solution containing 30 µL of hexane-perfluorohexane droplet phase was loaded into sample holder to create a monolayer of Janus droplet that covered the whole viewing window. The sample holder and solution of the Janus droplets were kept below 20° C., the $T_c$ of hexane-perfluorohexane mixture, during the sensing of ConA and image acquisition.

Model system: Sensing of ConA. ConA was dissolved in HEPES buffer solution with final concentration of 0.5 mg mL$^{-1}$ and used as the analyte. 10 µL of ConA solution was added using a micropipette to the sample holder containing Janus droplets. Solution was then swirled gently and agglutination of Janus droplets were observed within seconds. Image were recorded before and after adding ConA solution. An increasing volume (up to 40 µL) of ConA solution were added afterwards to get a correlation between agglutination level and analyte concentration. Agglutination level were analyzed both qualitatively and quantitatively as described below.

Surface Chemistry

Fabrication of DNA functionalized surface. Glass substrates were cleaned by sonication in acetone and isopropyl alcohol for 5 min each to remove dust. After drying completely, the glass substrates were immersed in piranha solution ($H_2SO_4:H_2O_2$, 1:1, v/v) for 1 h, rinsed thoroughly with distilled water, and then dried under $N_2$. The glass substrates were then immersed and reacted with a toluene solution of trichlorosilane linker terminated with an N-hydroxysuccinimide (NHS) for 1 h to form NHS covalently functionalized glass substrates. Afterwards, a solution of 10 µM ssDNA dissolved in a sodium tetraborate buffer at pH 9 was reacted to form an amide bond, which attach the ssDNA onto surface of the glass slides. ssDNA was functionalized with alkyl chain to form a surfactant molecule. Janus droplets residing on the surface of ssDNA functionalized glass substrate were tilted against gravity. A solution of the complementary strand dissolved in 0.25 M NaCl solution was added to Janus droplets to hybridize the DNA strands. Janus droplets were released from the glass substrate to be aligned with gravity at areas where DNA strands were hybridized. X-ray photoelectron spectroscopy was used to analyze the elements on glass substrates to ensure successful functionalization of ssDNA.

Detection

Sample preparation for detection. For both qualitative and quantitative methods of detection, Janus droplets were imaged in a stainless steel sample holder. For qualitative detection, a two-dimensional QR code (1 cm×1 cm) was placed 1 cm below the viewing window of the analysis chamber. For quantitative detection, a white background was used instead of the QR code to provide contrast. The analysis chamber and the solution of the Janus droplets were kept in an ice bath, well below the $T_c$ of the hexane-perfluorohexane mixture to maintain the morphology of the Janus droplets.

Qualitative analysis using QR code. Qualitative analysis was performed using the QR code from unmagnified images taken from the smartphone. The distance from the phone to the analysis chamber containing the Janus droplets was approximately 10 cm. The exact distance was calibrated by the image processing software by using the known dimension of the QR code (1 cm×1 cm). The binary response measured was whether the QR code could be read via the software. If the QR code was readable, the Janus droplets were considered not agglutinated, and vice versa.

Image acquisition for quantitative analysis. To acquire the low-magnification images for quantitative analysis, an adaptor with magnifying lenses was adapted onto the smartphone. With this modification, optical micrographs with 4× and 10× magnification were obtained. The working distance from the smartphone to the analysis chamber was 1 cm. The working distance and the dimension of the images were calibrated by the calibrated marking underneath the analysis chamber with 10 μm tick marks. The image processing software then pre-processed the captured images by transforming them into greyscale images and adjusting the brightness and contrast to the reference image of blank analysis chamber. For each sample, 100 pictures were taken, forming a 10×10 array of images to span the majority of the area of the analysis chamber.

Identification of overlapping Janus droplets. From the pre-processed images with 10× magnification (greyscale images with adjusted brightness and contrast), the image processing program first estimated the range of diameters of the Janus droplets by using the calibrated marking underneath the analysis chamber. The program then sought out and mapped the centers and calculated the diameters of every Janus droplet. This process was done by a modified method based on the Circle Hough Transform. With the coordinates of the centers and the diameters of the Janus droplets, the program then evaluated overlapping droplets. Specifically, if the distance between two centers of two droplets was smaller than the sum of the two radii, the droplets were considered overlapping. Using this logic, the program could effectively map out the number of overlapping neighbors for every identified droplet.

Identification of droplet complexes. A Janus droplet was considered to be a part of a droplet complex if the number of its overlapping neighbor exceeded three. This threshold was set in some cases to prevent over-counting of the droplets at the edges of the droplet complexes and accidental overlapping of droplets. This measurement was further collaborated by the analysis based on the optical intensity. The area occupied by the agglutinated droplet complexes was then calculated.

Analysis of changes in optical intensity. Using the pre-processed images of 4× magnification (greyscale images with adjusted brightness and contrast), the program first applied the adaptive thresholding algorithm to distinguish the darker edges of the Janus droplets from the droplet complexes with tilted particles. More specifically, the program ignored the edges of the droplets that have inherent low-light intensity and only sought the area of droplet complexes. A threshold was set using areas with light intensity of less than 45% of the brightest regions to be considered part of the droplets complex. From this information, the area occupied by the droplet complexes was then calculated.

Detection of Zika Virus

Zika is a vector-borne flavivirus which has emerged as a global health priority in recent years. Although Zika virus infections typically only cause mild febrile symptoms in adults, the virus can be passed from infected pregnant women to their fetuses and has been linked to severe birth defects such as microcephaly. Additionally, Zika virus has been connected to neurological disorders in adults, including Guillain-Barré Syndrome. No approved vaccines or treatments currently exist for Zika virus; as a consequence rapid accurate detection of Zika virus is essential to control epidemics and reduce the risk of these neurological complications. In recent years, many researchers have focused on developing assays for the detection of Zika virus, including polymerase chain reaction (PCR) and antibody based assays. Additionally, Zika virus detection using RNA amplification and CRISPR/Cas9 in rapid and low-cost sensors has been reported to be used in pandemic regions. However, there is still a need for a sensing assay with high stability, lower cost, and less reliance on specialized instrumentation, which could become essential in areas with endemic transmission of Zika.

This example is generally related to the use of Janus for the detection of the Zika virus. In this example, detection is conducted via recognition of protein NS1, a non-structural hexameric biomarker which plays a role in pathogenesis and immune evasion, although other proteins are also possible. This agglutination assay for the detection of this analyte that is generally robust, low cost, and readily multiplexed.

Selectivity and sensitivity in this emulsion agglutination assay is generally determined by the specific binding activity to the target analyte and the translation of analyte binding to an agglutinated complex, which in turn changes optical transmission through a layer of emulsion droplets. To conjugate thiol containing receptor biomolecules, a maleimide-functionalized polystyrene-b-polyacrylic acid (P1-MA) was employed as the surfactant. Using this construction variants of the hyperthermophilic binding protein were conjugated, reduced-charged Sso7d (rcSso7d). This selection is attractive as the rcSso7d protein is a viable replacement for antibodies in immunoassays, as a result of its intrinsic thermal and chemical stability, ease of large-scale biomanufacturing, and a versatile binding face. This protein scaffold can further be engineered to have high affinity for specific target proteins. To optimize an agglutination assay, the streptavidin-binding rcSso7d variant (rcSso7d-SA) was used for the protein-protein recognition. In addition, two novel optical transduction methods, which can be readily instrumented, were prepared for the quantification of the analyte. This optimization allowed for the efficient integration of the rcSso7d Zika NS1 binding variant (rcSso7d-ZNS1) into the assay format. The optimized system demonstrates a detection limit of 100 nM for the Zika NS1 protein. Emulsion droplet disposable assays based on the constructions presented herein have the advantage of thermally stable recognition elements, simple detection, and the avoidance of nucleic acid extractions that often require a trained technician.

Figures 10A, 10B:
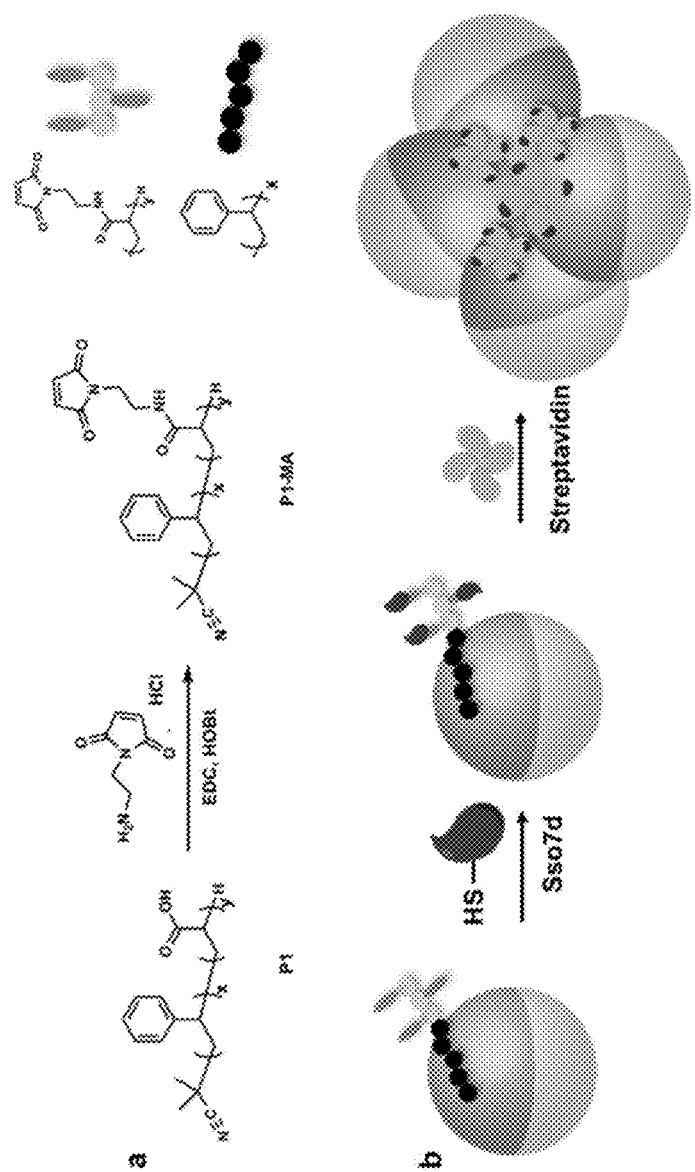
FIGS. 10A-10B show functionalization of the droplets with the polymer surfactant, according to one set of embodiments.

Gallic acid derived surfactants may be used for droplet bioconjugation. These surfactants exhibited good stability and displayed sensor behavior by triggering droplet morphology changes. However, the gallic acid derived surfactants may not, in some cases, have the anchoring strength necessary to hold multiple droplets together in an agglutination assay. The block co-polymer anchor, polystyrene-b-polyacrylic acid (P1) displayed a good connection strength between the protein and droplets. The acrylic acid block in P1 was functionalized with maleimide-$NH_2$ to form P1-MA (FIG. 10A). P1-MA was dissolved in the hydrocarbon phase and behaves as a hydrocarbon/water (H/W) interfacial active agent. Without wishing to be bound by theory, this generally positions the maleimide group at the H/W interphase, enables the maleimide-thiol bioconjugation of cysteine-bearing proteins, and the production of protein-functionalized emulsion droplets.

To produce agglutination with the emulsion droplets, protein-protein interactions are used, wherein the recognition protein rcSso7d is immobilized on the droplets. For this construction, the previously engineered rcSso7d-SA was further genetically modified with a cysteine residue on the N-terminus for bioconjugation to the droplet. The cysteine-modified rcSso7d-SA was then covalently linked to the hydrocarbon-water (H/W) interface via a maleimide-thiol conjugate addition reaction. The addition of the tetravalent streptavidin to the rcSso7d-SA functionalized droplets triggers agglutination by linking rcSso7d from different droplets together (FIG. 10B). The agglutination was observed within 30 min of the addition of the streptavidin.

Figure 11:
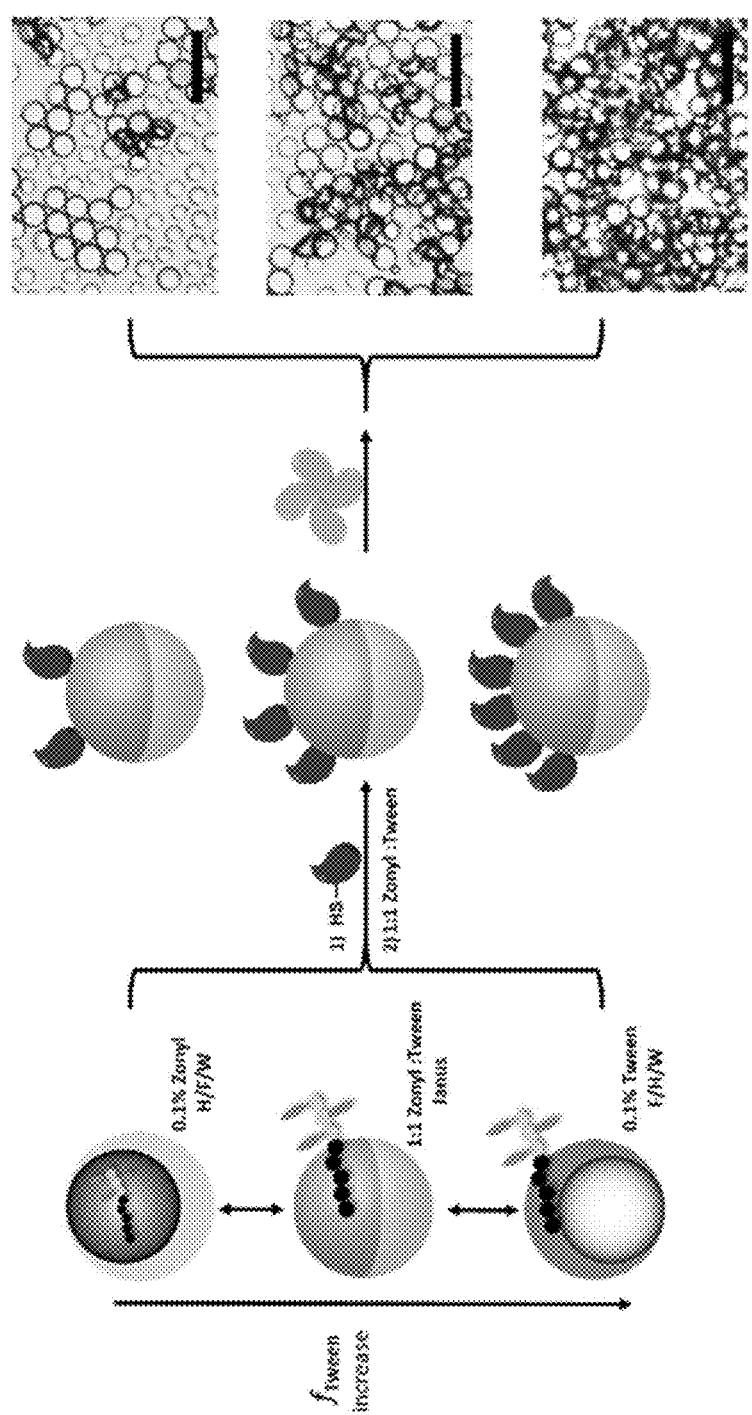
FIG. 11 shows droplets starting at different morphologies, namely H/F/W, Janus and F/H/W functionalized with cysteine engineered rcSso7d, according to one set of embodiments. The continuous phase was exchanged to tune the morphology into the Janus format, followed by the addition of 10 μL of 1 mg mL$^{-1}$ (0.36 μM) streptavidin. Note that a higher degree of agglutination is observed with droplets prepared at the higher Tween 20 concentrations. The scale bars in the optical micrographs are 100 μm.

The amount of rcSso7d-SA conjugated to the droplet H/W interface is generally related to droplet morphology during the reaction. To optimize the level of functionalization of rcSso7d-SA for agglutination, three initial morphologies (1) hydrocarbon-in-fluorocarbon-in-water (H/F/W), (2) Janus, and (3) fluorocarbon-in-hydrocarbon-in-water (F/H/W) were created by tuning the proportions of the continuous phase surfactants. As shown in FIG. 11, each droplet initially has a different morphology and consequently a different surface area at the H/W interface for bioconjugation. After rcSso7d-SA functionalization, each droplet type was switched to the same morphology (Janus state) by exchanging the continuous phase surfactant solution in order to compare the relative agglutination responses. Streptavidin (0.36 μM) was added to agglutinate the Janus droplets. As shown in the micrographs in FIG. 11, the droplets that were functionalized in a F/H/W morphology displayed higher agglutination levels. This result indicates that the increased surface area at the hydrocarbon/water interface facilitates the functionalization with rcSso7d and increases the agglutination sensitivity. Although a higher concentration of Tween 20 is used for the F/H/W morphology, the P1-MA molecule exhibits stronger surfactant behavior and effectively competes to partition at the H/W interface for an optimal maleimide-thiol conjugation reaction. Given the greater degree of agglutination achieved using droplets conjugated in the F/H/W morphology, this configuration was used for rcSso7d functionalization in all of the following studies.

Figures 12A, 12B, 12C:
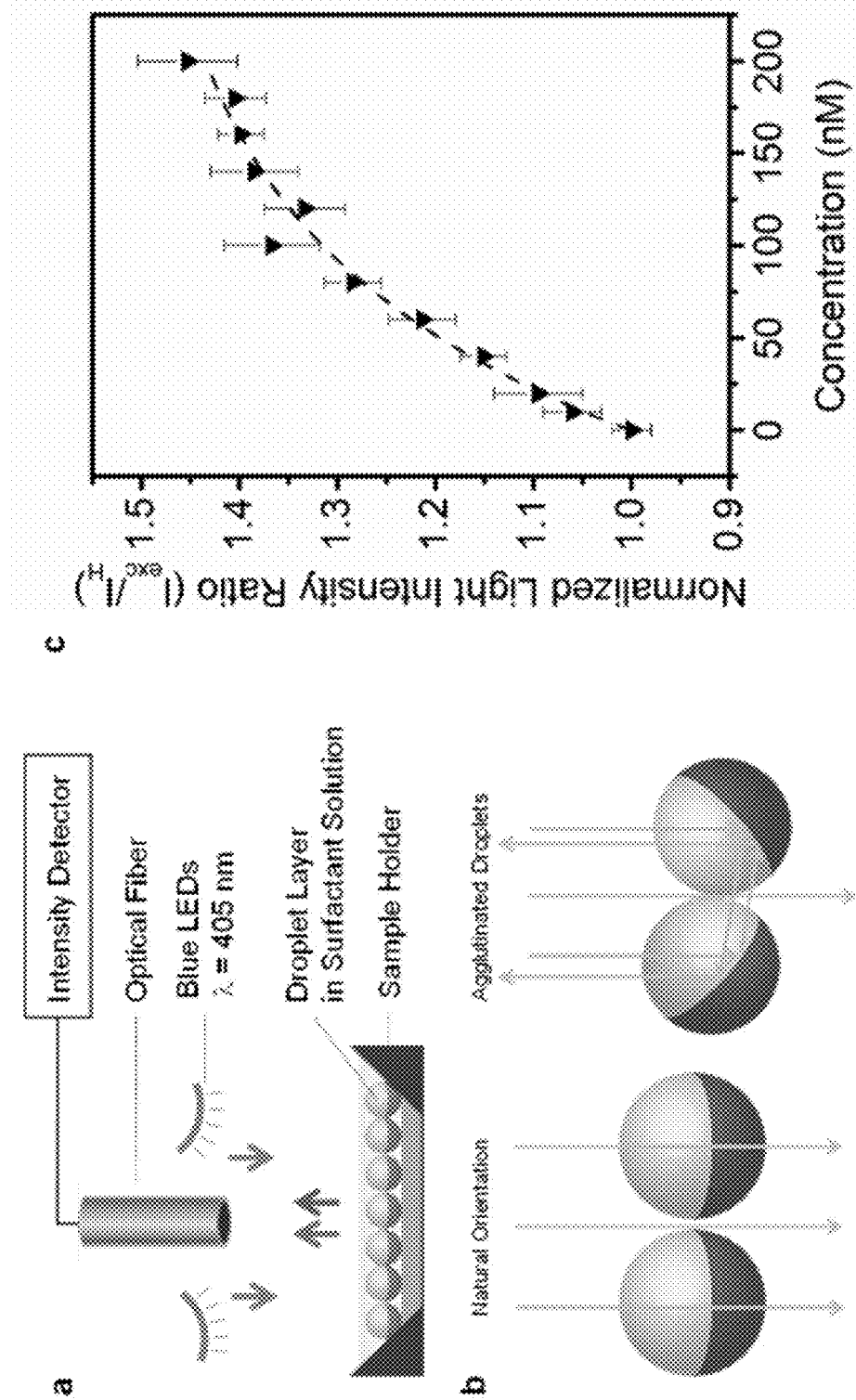
FIGS. 12A-12C show optical detection using the backscattering scheme, according to one set of embodiments.
Figure 15:
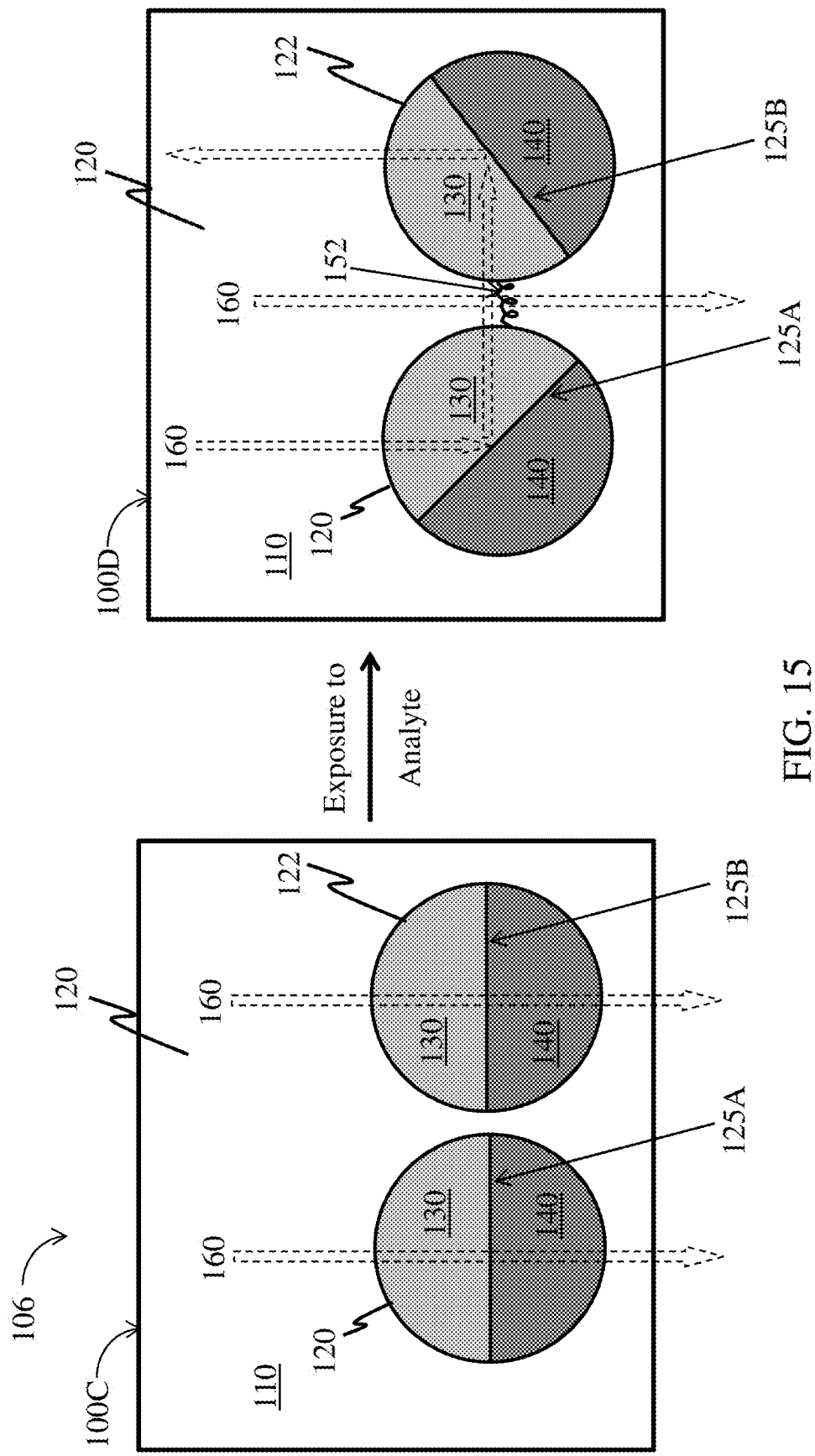
FIG. 15 is a schematic diagram of backscattering (e.g., retroreflection), according to one set of embodiments.

Having established this emulsion assay for the detection of small quantities of streptavidin, a quantitative optical read-out of droplet agglutination was created. Without wishing to be bound by theory, Multi-compartment colloids have intrinsic optical properties as a result of the differing refractive indices of the constituent phases. Double emulsion droplets are tuneable lenses with optical properties that vary with the droplet morphology. The refractive index contrast and curvature of each interface contribute to the lenses' ability to focus or scatter. The strong variations in the light transmission properties of Janus droplets before and after agglutination are displayed in the optical micrographs of FIG. 11. Increases in the fraction of agglutinated (tilted) droplets causes more scattering of the incoming light, which can be measured in transmission or backscattering modes normal to the droplet layer. To produce a system displaying large optical effects, we chose a solvent combination with a relatively large refractive index (RI) contrast, diethylbenzene (RI: 1.49) for the hydrocarbon phase and HFE 7500 (RI: 1.29) for the fluorocarbon phase. Depending on the angle of the internal H/F interface, the incoming light rays can intersect the internal H/F interface at angles below or above the critical angle: $\theta_c=60°$. As a result, depending on the droplet's morphology and the refractive index contrast, the incoming light could undergo total internal reflection (TIR). In this agglutination sensing scheme, the selectors were selectively immobilized at the hydrocarbon/water interphase, which leads to the aggregation of the high RI hydrocarbon phases. As a result of the surfaces and RI contrast, in the agglutinated state light can be backscattered in the upward direction, similar to a corner cube reflector (FIG. 12B and FIG. 15). In order to translate this light scattering effect into an applicable optical detection scheme, an optical fiber was positioned on top a droplet monolayer and recorded the light intensity (FIG. 12A). For reproducibility and for creating a ratiometric read-out of the degree of agglutination, a fluorescent dye (perylene; 1.5 mM) was added to the hydrocarbon phase and the intensity ratio of the excitation light ($I_{exc}$) to the reference perylene emission ($I_H$) was recorded. Increased tilting of the droplets leads to an increase of the backscattered light intensity. Depending on the concentration of streptavidin and therefore the degree of agglutination, this optical sensor scheme provides a ratiometric signal for quantitative measurements with maximum intensity increase of up to 50% (FIG. 12C).

Figures 13A, 13B, 13C:
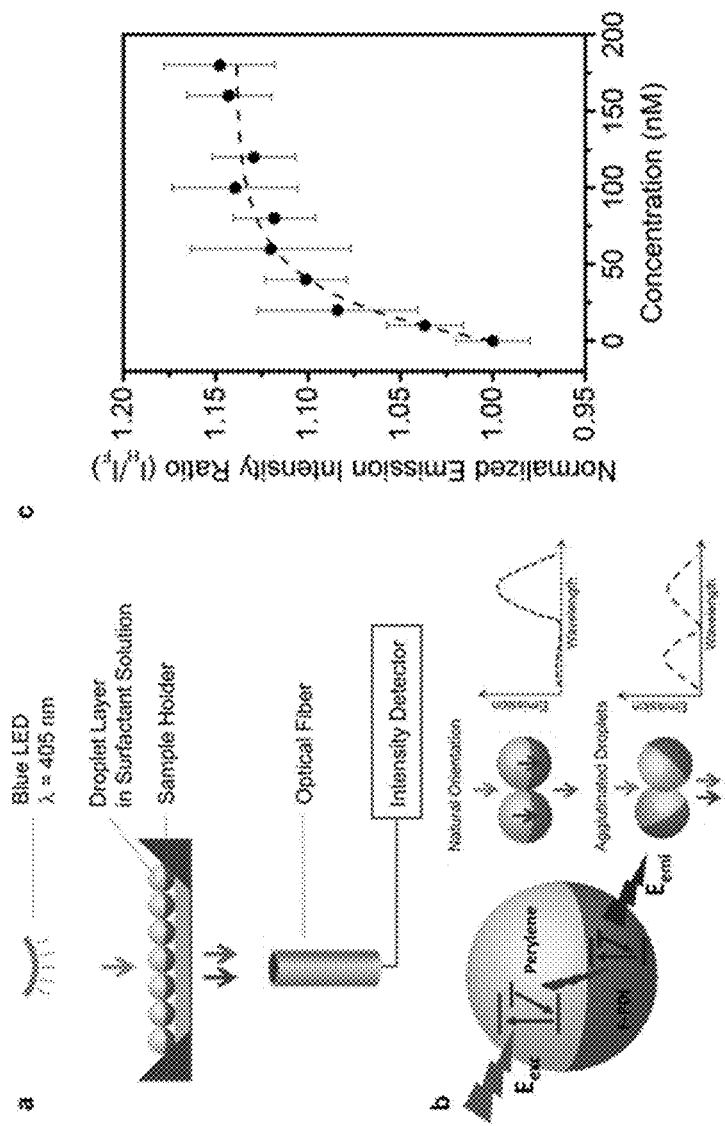
FIGS. 13A-13C show optical scheme using the inner filter effect, according to one set of embodiments.

In addition, an additional purely fluorescent based sensor read-out of droplet agglutination was created. This method provides a robust scheme, with the advantage of using multilayers of polydisperse droplets, more accurate ratiometric signals, and the possibility of multiplexing. In this scheme a second emissive dye (F-PDI) was dissolved in the fluorocarbon phase. Changes in droplet alignment in response to streptavidin were quantified by recording the ratio of the emission from two dyes in the hydrocarbon and the fluorocarbon phase (FIG. 13A). By targeted selection of the dyes, the emitted light of one of the dyes can be selectively attenuated via the inner filter effect depending on the orientation of the droplets. F-PDI exhibits absorption with a spectral overlap with the emission of a high band gap (blue light emitting) perylene dye in the hydrocarbon phase. The overall emission of the emulsion may be dominated, in some cases, by the red fluorophore if the droplets are arranged in their gravity aligned fashion because the emitted light from the perylene dye collected by the optical fiber has to pass through the phase with the F-PDI dye before exiting the droplet. The degree of agglutination is accompanied by a continuous increase of the emission of the perylene dye, as a result of the decreased path length though the absorbing fluorocarbon phase (FIG. 13B). As displayed in FIG. 13C, the detection of the ratio of perylene ($I_H$) and F-PDI ($I_F$) emission provide for precise correlation with the level of agglutination, which can be used to quantify analyte concentration. Similar to the backscattering scheme described above, higher concentrations of streptavidin produce saturation of the light intensity ratio. Both methods show similar analyte sensitivity, which is indicated by the slope of the curve at low concentration.

Figure 14:
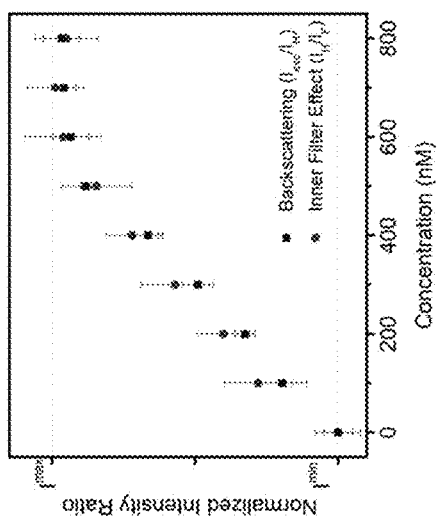
FIG. 14 shows a plot of normalized intensity ratio versus concentration for Zika detection using the backscattering and the inner filter effect, according to one set of embodiments.

The agglutination assay was then adapted for the detection of the polyvalent Zika NS1 protein using droplets conjugated to rcSso7d-ZNS1 via a cysteine at the N-terminus. The intensity curves reveal the sensitivity of the agglutination assay for Zika NS1 and the results are shown in FIG. 14. As a result of the lower binding strength of the Zika NS1 to the rcSso7d-ZNS1 as compared to the streptavidin to rcSso7d-SA, the reaction was equilibrated overnight, which allows for higher agglutination yields and the lowest limit of detection. The two optical schemes using the backscattering and inner filter effect are in agreement after normalization to the maximum (saturated) emission intensity, with a limit of detection of 100 nM.

In summary, an agglutination assay for the sensing of Zika NS1 protein at a limit of detection of 100 nM using two optical schemes that can be easily prototyped was described. A maleimide functionalized P1-MA polymer was used as the surface active agent to covalently link the hyperthermophilic rcSso7d protein to the surface of the droplets. The multivalent protein analyte Zika NS1 binds to surface bound rcSso7d groups to cause droplet agglutination. Robust ratiometric signals to detect agglutination were developed by incorporating dyes in the droplets and detecting backscattered/emitted light, or multiple emissions modulated by an inner filter effect. This emulsion agglutination assay offers low power requirements without complicated labelling and nucleic acid handling. The assay is potentially suitable for use in remote locations without access to expensive equipment and trained personnel to identify Zika virus infections as well as other pathogenic species.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A system comprising:
    a plurality of Janus droplets associated with binding moieties to an analyte, the plurality of Janus droplets comprising an interface between a first phase and a second phase of the droplets, the binding moiety and analyte selected such that when the analyte binds to the binding moiety at least a portion of the plurality of Janus droplets are changed in orientation sufficient to change electromagnetic radiation interacting with the plurality of Janus droplets in a detectable manner, wherein the plurality of Janus droplets are optically transparent in a direction perpendicular to a surface of the interface in the first orientation, and wherein the analyte is a virus, a pathogen, or a bacterium.

2. A system as in claim 1, wherein upon binding to the analyte, at least a portion of the plurality of Janus droplets agglutinate.

3. A system as in claim 1, wherein, prior to binding to the analyte, the plurality of Janus droplets are oriented such that at least a portion of interfaces between a first phase and a second phase within each Janus droplet are aligned parallel with respect to one another.

4. A system as in claim 1, wherein, prior to the analyte binding to the binding moieties, the plurality of Janus droplets are physically and/or chemically bound to a surface.

5. A system as in claim 4, wherein, upon binding of the analyte to the binding moieties, at least a portion of the plurality of Janus droplets unbind from the surface.

6. An article, comprising:
    an outer phase; and
    a plurality of Janus droplets dispersed within the outer phase, the plurality of Janus droplets comprising an interface between a first phase and a second phase of the droplets,
    wherein at least a portion of the plurality of Janus droplets comprise an amphiphilic compound including at least one binding moiety to an analyte,
    wherein the analyte is a virus, a pathogen, or a bacterium,
    wherein, upon binding of the at least one binding moiety with the analyte, at least a portion of the plurality of Janus droplets change orientation, and
    wherein the plurality of Janus droplets are optically transparent in a direction perpendicular to a surface of the interface.

7. An article as in claim 6, wherein the plurality of Janus droplets is oriented such that at least a portion of interfaces between the first phase and the second phase within each Janus droplet are aligned parallel with respect to one another, wherein the alignment is by gravity.

8. An article as in claim 6, wherein the plurality of Janus droplets are substantively transmissive to electromagnetic radiation.

9. An article as in claim 6, wherein, upon binding of the at least one binding moiety with the analyte, the plurality of Janus droplets decrease in optical transmission.

10. An article, comprising:
    a surface;
    an outer phase deposited on at least a portion of the surface; and
    a plurality of Janus droplets dispersed within the outer phase, the plurality of Janus droplets comprising an interface between a first phase and a second phase of the droplets,
    wherein at least a portion of the plurality of Janus droplets comprise an amphiphilic compound including at least one binding moiety to an analyte, wherein the analyte is a virus, a pathogen, or a bacterium,
    wherein at least a portion of the plurality of Janus droplets are bound to the surface via the binding moiety, and
    wherein, upon exposure of the plurality of Janus droplets to the analyte, at least a portion of Janus droplets change orientation, and
    wherein the plurality of Janus droplets are optically transparent in a direction perpendicular to a surface of the interface.

11. An article as in claim 10, wherein at least a portion of the plurality of Janus droplets are oriented such that an interface between a first phase and a second phase within each Janus droplet are not aligned parallel to the surface.

12. An article as in claim 10, wherein, upon exposure of the plurality of Janus droplets to the analyte, at least a portion of Janus droplets unbind from the surface.

13. An article as in claim 12, wherein the article is substantively visible-light transmissive after exposure to the plurality of Janus droplets to the analyte.

14. An article as in claim 10, wherein, upon exposure of the plurality of Janus droplets to the analyte, the plurality of Janus droplets increase in optical transmission.

15. A system, comprising:
    an article as in claim 10;
    a source of external energy applicable to the composition to generate a determinable signal; and
    a detector positioned to detect the signal.

16. A system as in claim 15, wherein the signal comprises electromagnetic radiation.

* * * * *

UNITED STATES PATENT AND TRADEMARK OFFICE
CERTIFICATE OF CORRECTION

| | |
|---|---|
| PATENT NO. | : 12,061,194 B2 |
| APPLICATION NO. | : 17/545979 |
| DATED | : August 13, 2024 |
| INVENTOR(S) | : Timothy Manning Swager et al. |

It is certified that error appears in the above-identified patent and that said Letters Patent is hereby corrected as shown below:

In the Specification

At Column 1, Lines 21-24, Statement of Government Support:
"This invention was made with Government support under Grant No. R01-GM095843 awarded by the National Institutes of Health. The Government has certain rights in the invention."

Should be:
--This invention was made with government support under GM095843 awarded by the National Institutes of Health. The government has certain rights in the invention.--

Signed and Sealed this
Fifteenth Day of October, 2024

Katherine Kelly Vidal
*Director of the United States Patent and Trademark Office*